(12) United States Patent
Tolan et al.

(10) Patent No.: US 8,298,796 B2
(45) Date of Patent: Oct. 30, 2012

(54) METHOD FOR THE PRODUCTION OF GLUCOSE FROM LIGNOCELLULOSIC FEEDSTOCKS

(75) Inventors: Jeffrey S. Tolan, Ottawa (CA); Brian Foody, Ottawa (CA)

(73) Assignee: Iogen Energy Corporation, Ottawa, Ontario (CA)

( * ) Notice: Subject to any disclaimer, the term of this patent is extended or adjusted under 35 U.S.C. 154(b) by 495 days.

(21) Appl. No.: 12/686,485

(22) Filed: Jan. 13, 2010

(65) Prior Publication Data
US 2010/0184151 A1 Jul. 22, 2010

Related U.S. Application Data

(60) Provisional application No. 61/144,511, filed on Jan. 14, 2009.

(51) Int. Cl.
| | |
|---|---|
| *C12P 19/02* | (2006.01) |
| *C12P 19/00* | (2006.01) |
| *C12P 19/14* | (2006.01) |
| *C12P 7/04* | (2006.01) |
| *C12P 7/08* | (2006.01) |
| *C12P 7/10* | (2006.01) |

(52) U.S. Cl. ............ 435/105; 435/72; 435/99; 435/157; 435/163; 435/165

(58) Field of Classification Search ............... 435/72, 435/99, 105, 157, 163, 165
See application file for complete search history.

(56) References Cited

U.S. PATENT DOCUMENTS

| | | |
|---|---|---|
| 4,425,433 A | 1/1984 | Neves |
| 5,628,830 A | 5/1997 | Brink |
| 5,693,296 A | 12/1997 | Holtzapple et al. |
| 5,865,898 A | 2/1999 | Holtzapple et al. |
| 6,043,392 A | 3/2000 | Holtzapple et al. |
| 6,927,048 B2 | 8/2005 | Verser et al. |
| 2006/0188965 A1 | 8/2006 | Wyman et al. |
| 2008/0102502 A1 | 5/2008 | Foody et al. |

FOREIGN PATENT DOCUMENTS

| | | |
|---|---|---|
| WO | 2006/128304 | 12/2006 |
| WO | 2009/026707 | 3/2009 |

OTHER PUBLICATIONS

Chang et al., "Lime Pretreatment of Crop Residues Bagasse and Wheat Straw", Applied Biochemistry and Bitoechnology, vol. 74 (1998) 135-59.
Yang et al., "Pretreatment: the key to unlocking low-cost cellulosic ethanol", Biofuels, Bioproducts & Biorefining, vol. 2, No. 1 (2008) 26-40.

*Primary Examiner* — Herbert J Lilling
(74) *Attorney, Agent, or Firm* — Fitzpatrick, Cella, Harper & Scinto

(57) ABSTRACT

A method for producing glucose from a lignocellulosic feedstock is provided. The method comprises pretreating the lignocellulosic feedstock with acid to produce a pretreated feedstock composition. A calcium-containing stream is provided that comprises calcium that is obtained from the lignocellulosic feedstock and a calcium carbonate-containing stream is obtained by precipitation of the calcium from the calcium-containing stream. The pH of the pretreated feedstock is adjusted with (a) the calcium carbonate-containing stream; (b) a calcium hydroxide-containing stream that is derived from said calcium carbonate-containing stream by subjecting said calcium carbonate-containing stream to calcination; or (c) a combination of the calcium carbonate-containing stream and the calcium hydroxide-containing stream. The pH adjustment results in a neutralized pretreated lignocellulosic feedstock having a pH between about 3 and about 9 and enzymatic hydrolysis of the neutralized, pretreated lignocellulosic feedstock is then conducted with cellulase enzymes to produce the glucose.

20 Claims, 11 Drawing Sheets

METHOD FOR THE PRODUCTION OF GLUCOSE FROM LIGNOCELLULOSIC FEEDSTOCKS

RELATED APPLICATIONS

This application claims the priority benefit of a provisional application entitled "Improved Method for the Production of Glucose from Lignocellulosic Feedstocks" Ser. No. 61/144,511 filed Jan. 14, 2009, the entire contents of which are incorporated by reference herein.

FIELD OF THE INVENTION

The present invention relates to a method for producing glucose from a lignocellulosic feedstock. More specifically, the present invention relates to a method for producing glucose from a lignocellulosic feedstock involving acid pretreatment and cellulose hydrolysis.

BACKGROUND OF THE INVENTION

Fuel ethanol is currently produced from feedstocks such as corn starch, sugar cane, and sugar beets. However, the potential for production of ethanol from these sources is limited as most of the farmland which is suitable for the production of these crops is already in use as a food source for humans. Furthermore, the production of ethanol from these feedstocks has a negative impact on the environment because fossil fuels used in the conversion process produce carbon dioxide and other byproducts.

The production of ethanol from cellulose-containing feedstocks, such as agricultural wastes, grasses, and forestry wastes, has received much attention in recent years. The reasons for this are that these feedstocks are widely available and inexpensive and their use for ethanol production provides an alternative to burning or landfilling lignocellulosic waste materials. Moreover, a byproduct of cellulose conversion, lignin, can be used as a fuel to power the process instead of fossil fuels. Several studies have concluded that, when the entire production and consumption cycle is taken into account, the use of ethanol produced from cellulose generates close to nil greenhouse gases.

The three primary constituents of lignocellulosic feedstocks are cellulose, which comprises 30% to 50% of most of the key feedstocks; hemicellulose, which comprises 15% to 35% of most feedstocks; and lignin, which comprises 15% to 30% of most feedstocks. Cellulose and hemicellulose are comprised primarily of carbohydrates and are the source of sugars that can potentially be fermented to ethanol. Lignin is a phenylpropane lattice that is not converted to ethanol.

Cellulose is a polymer of glucose with beta-1,4 linkages and this structure is common among the feedstocks of interest. Hemicellulose has a more complex structure that varies among the feedstocks. For the feedstocks which are typically of interest, the hemicellulose typically consists of a backbone polymer of xylose with beta-1,4 linkages, with side chains of 1 to 5 arabinose units with alpha-1,3 linkages, or acetyl moieties, or other organic acid moieties such as glucuronyl groups.

The first process step for converting lignocellulosic feedstock to ethanol involves breaking down the fibrous material. The two primary processes are acid hydrolysis, which involves the hydrolysis of the feedstock using a single step of acid treatment, and enzymatic hydrolysis, which involves an acid pretreatment followed by hydrolysis with cellulase enzymes.

In the acid hydrolysis process, the feedstock is subjected to steam and a mineral acid, such as sulfuric acid, sulfurous acid, hydrochloric acid, or phosphoric acid. The temperature, acid concentration and duration of the acid hydrolysis are sufficient to hydrolyze the cellulose and hemicellulose to their monomeric constituents, which is glucose from cellulose and xylose, galactose, mannose, arabinose, acetic acid, galacturonic acid, and glucuronic acid from hemicellulose. If sulfuric acid is employed, it can be concentrated (25-80% w/w) or dilute (3-8% w/w). The resulting aqueous slurry contains unhydrolyzed fiber that is primarily lignin, and an aqueous solution of glucose, xylose, organic acids, including primarily acetic acid, but also glucuronic acid, formic acid, lactic acid and galacturonic acid, and the mineral acid. Although this process produces ethanol, the yield is low due to the non-selective nature of the acid hydrolysis.

In the enzymatic hydrolysis process, the steam temperature, mineral acid (typically sulfuric acid) concentration and treatment time of the acid pretreatment step are chosen to be milder than that in the acid hydrolysis process. Similar to the acid hydrolysis process, the hemicellulose is hydrolyzed to xylose, galactose, mannose, arabinose, acetic acid, glucuronic acid, formic acid and galacturonic acid. However, the milder pretreatment does not hydrolyze a large portion of the cellulose, but rather increases the cellulose surface area as the fibrous feedstock is converted to a muddy texture. The pretreated cellulose is then hydrolyzed to glucose in a subsequent step that uses cellulase enzymes.

Prior to the addition of enzyme, the pH of the acidic feedstock is adjusted to a value that is suitable for the enzymatic hydrolysis reaction. Typically, this involves the addition of alkali to a pH of between about 4 and about 6, which is the optimal pH range for cellulases, although the pH can be higher if alkalophilic cellulases are used and lower if acidic cellulases are used. Alkali that are most commonly used to adjust the pH of the acidified pretreated feedstock prior to hydrolysis by cellulase enzymes are ammonia, ammonium hydroxide and sodium hydroxide, although the use of carbonate salts such as potassium carbonate, potassium bicarbonate, sodium carbonate and sodium bicarbonate has also been contemplated. (See WO 2006/128304, Foody et al.).

U.S. Pat. No. 5,628,830 (Brink) discloses the use of calcium carbonate to adjust the pH of an aqueous sugar solution containing xylose, glucose, mannose and galactose arising from acid hydrolysis of lignocellulosic feedstock. After pH adjustment of the aqueous sugar solution, the solution is submitted to fermentation. However, Brink's process employs full acid hydrolysis, which suffers from the disadvantage discussed above.

One shortcoming of processing lignocellulosic feedstocks to produce glucose is the large amounts of alkali that are required to adjust the pH of the acid pretreated feedstock prior to enzymatic hydrolysis with cellulase enzymes. The addition of alkali adds significant cost to the process. In addition, the alkali reacts with the acid to produce salt, which must be processed or disposed of.

U.S. Pat. No. 4,425,433 (Neves) discloses the use of sodium carbonate or sodium bicarbonate to neutralize an acidic feedstock slurry containing glucose, which slurry is produced by acid hydrolysis of the cellulose and hemicellulose components of the feedstock. After the neutralization, the acidic slurry or "wort", as referred to therein, is submitted to fermentation. However, a disadvantage of this process is that the amount of sodium carbonate and sodium bicarbonate required for the pH adjustment would add significant cost to the process and produce a large amount of salt to be disposed of.

U.S. Pat. No. 6,927,048 (Verser et al.) discloses a process in which calcium carbonate and an amine or an alcohol are added during the fermentation of glucose to acetic acid. The calcium carbonate controls the pH while the amine or alcohol complexes with the acetic acid. After the fermentation, the calcium carbonate is precipitated by the addition of carbon dioxide and then recovered from the fermentation broth. The recovered calcium carbonate is then reused in the subsequent fermentation. Thus, Verser et al. does not address the reduction of alkali use during the pretreatment and neutralization of a lignocellulosic feedstock.

U.S. Pat. No. 6,043,392 (Holtzapple et al.) also does not address reducing alkali usage during a neutralization conducted after acid pretreatment of a lignocellulosic feedstock. Rather, Holtzapple discloses a process that involves lime (alkali) treatment of lignocellulosic feedstocks with a subsequent fermentation step to produce volatile fatty acids (VFAs), followed by a thermal conversion of the VFAs to produce ketones. Calcium carbonate may be produced during an evaporation step involving carbon dioxide addition prior to thermal conversion of the VFAs. The calcium carbonate is recycled to the fermentor to neutralize acids that are produced by the fermentation or is burned in a lime kiln to produce lime which may be used in the lime treatment.

Similarly, U.S. Pat. No. 5,693,296, also to Holtzapple, discloses a process involving treating biomass with calcium oxide or hydroxide, followed by carbonating the pretreated material to form calcium carbonate or bicarbonate. The calcium carbonate may be heated in a lime kiln to form calcium oxide, which can be hydrated to form calcium hydroxide, which, in turn, can be used to treat the biomass. Thus, this process also does not address reducing chemical usage during a neutralization of an acid pretreated feedstock in the production of glucose. A similar process is disclosed by Chang et al., 1998, Applied Biochemistry and Biotechnology, 74:135-159.

US 2006/0188965 (Wyman and Lloyd) discloses a process involving acid pretreatment of cellulosic biomass. The acid-pretreated feedstock slurry is then mixed with a lime solution to impart a pH of 10 to 11, followed by the addition of sulfuric acid to adjust the pH into a range of 5-7 prior to cellulose hydrolysis by cellulase. Following the enzymatic hydrolysis, a fermentation of the hydrolyzed material is carried out to produce alcohol, which is then concentrated by distillation. Remaining liquids and/or solids from the distillation are subjected to a recycle processing step to filter fine particulates. The resulting material is then sent back to the acid pretreatment, along with lignocellulosic material fed to the process. However, the recycling of this material back to pretreatment does not reduce the amount of alkali used to neutralize the pretreated cellulose.

At present, none of the prior art addresses operating an efficient and economical process for hydrolyzing lignocellulosic feedstocks to glucose, while decreasing alkali usage. The development of an efficient process to decrease alkali usage remains a critical requirement to convert a lignocellulosic feedstock to glucose.

SUMMARY OF THE INVENTION

The present invention overcomes several disadvantages of the prior art by taking into account the difficulties encountered in steps carried out during the processing of lignocellulosic feedstock to obtain fermentable sugar, namely glucose.

It is an object of the invention to provide an improved method for producing glucose from a lignocellulosic feedstock.

The present invention relates to a process in which a recycle stream comprising calcium carbonate, calcium hydroxide (referred to herein as calcium carbonate-containing and calcium hydroxide-containing streams, respectively), or a combination thereof, is used to adjust the pH of an acid pretreated lignocellulosic feedstock to a value amenable to cellulase enzymes. A primary feature of the invention is that the calcium in the calcium carbonate-containing stream or the calcium hydroxide-containing stream (or a combination thereof) used for the pH adjustment arises from calcium that is native to the lignocellulosic feedstock. Since the calcium arises from the feedstock itself, the process of the invention can lead to significant reductions in the amount of alkali that would otherwise be required to neutralize the pretreated feedstock. Alkali usage represents a significant cost of producing glucose from lignocellulosic feedstocks and the high level of alkali use has limited the economic viability of the lignocellulosic conversion process. Furthermore, the large amount of alkali leads to a high level of salt production, which must be processed or disposed of. As a result, the present invention is a significant improvement to the economics of lignocellulosic conversion processes and accordingly represents a major step forward in the commercialization of such processes.

According to the invention, the calcium carbonate-containing stream or the calcium hydroxide-containing stream is obtained by the precipitation of calcium from any calcium-containing stream arising from the process, given that the calcium in the stream arises from the feedstock. That is, the calcium-containing stream can be, or can be derived from, any stream resulting from the processing of the lignocellulosic feedstock to produce glucose. Preferably, the invention excludes processes involving recovery of lime that is added to the feedstock.

Thus, the present invention provides a method for processing a lignocellulosic feedstock to produce glucose, said method comprising the steps of:

(i) pretreating the lignocellulosic feedstock with acid to produce a composition comprising a pretreated feedstock;

(ii) providing a calcium-containing stream that comprises calcium that is obtained from the lignocellulosic feedstock;

(iii) producing a calcium carbonate-containing stream that is obtained by precipitation of said calcium from the calcium-containing stream;

(iv) adjusting the pH of a stream comprising the pretreated feedstock with
  (a) the calcium carbonate-containing stream;
  (b) a calcium hydroxide-containing stream that is derived from said calcium carbonate-containing stream by subjecting said calcium carbonate-containing stream to calcination; or
  (c) a combination of the calcium carbonate-containing stream and the calcium hydroxide-containing stream, wherein said adjusting of the pH of said stream comprising the pretreated feedstock produces a neutralized, pretreated lignocellulosic feedstock having a pH between about 3 and about 9 and wherein the pH of the neutralized, pretreated lignocellulosic feedstock thus produced is greater than the pH of the composition comprising pretreated feedstock produced in step (i); and (v) carrying out enzymatic hydrolysis of said neutralized, pretreated lignocellulosic feedstock with cellulase enzymes to produce the glucose.

The lignocellulosic feedstock may be selected from the group consisting of corn stover, soybean stover, corn cobs, rice straw, rice hulls, corn fiber, wheat straw, barley straw, canola straw, oat straw, oat hulls and combinations thereof.

Since many feedstocks of interest also contain magnesium, magnesium precipitation may occur in addition to the calcium precipitation. Thus, according to one embodiment of the invention, the calcium-containing stream contains magnesium that is obtained from the feedstock and magnesium carbonate is produced together with calcium carbonate by precipitation of the magnesium.

The pretreating may be conducted to hydrolyze at least a portion of hemicellulose present in the feedstock and increase accessibility of cellulose in the feedstock to being hydrolyzed with said cellulase enzymes. The pretreating is preferably conducted at a temperature of between about 160° C. to about 280° C. A preferred pH range for the pretreatment is between 0.4 and 3.0. Sulfuric acid is an example of a preferred acid for the pretreatment.

The calcium-containing stream from which the calcium is precipitated may be a sugar stream containing glucose, xylose, or a combination thereof, a still bottoms stream resulting from fermenting the glucose produced in step (v) to produce a fermentation broth comprising a fermentation product, distilling the fermentation broth to obtain a stream containing a concentrated fermentation product and the still bottoms stream, or a stream resulting from combining the sugar stream and the still bottoms stream. The calcium-containing stream may also be derived from any one of these streams.

According to another embodiment of the invention, a stream comprising calcium obtained from the lignocellulosic feedstock and resulting from processing of the lignocellulosic feedstock is obtained, which stream is selected from a sugar stream comprising glucose, xylose, or a combination thereof, a still bottoms stream, a combination of these streams, and a stream derived from any one of these streams. This stream comprising calcium is then passed through an ion exchange resin to reduce the concentration of calcium therein. The ion exchange resin may then be regenerated to produce a stream comprising a soluble calcium salt. This stream, which comprises the soluble calcium salt, is the calcium-containing stream that is then subjected to the precipitation.

The sugar stream, or the stream derived therefrom, passed through the ion exchange resin may be obtained from the composition comprising the pretreated lignocellulosic feedstock, either subsequent to the step of pretreating and prior to the step of enzymatically hydrolyzing, although the sugar stream can also be derived from other stages of the process.

The ion exchange resin may be a cation exchange resin. According to one embodiment of the invention, the cation exchange resin is a chelating resin. The ion exchange resin may be regenerated with acid, one or more soluble salts, or a combination thereof. If an acid is used, it is preferably hydrochloric acid. The one or more soluble salts may be selected from the group consisting of potassium chloride, ammonium chloride, sodium chloride and a combination thereof.

A stream containing sugar may be obtained from passage of the sugar stream, the still bottoms, a stream resulting from combining the sugar stream and the still bottoms stream, or a stream derived from any one of these streams, through the ion exchange resin. This sugar-containing stream, or a stream derived therefrom, may be fermented to produce an alcohol, a sugar alcohol, an organic acid, or a combination thereof.

The precipitation of calcium from the calcium-containing stream may comprise the addition of carbon dioxide, alkali, carbonate or biocarbonate salts, or a combination thereof, to the calcium-containing stream. The carbonate and bicarbonate salts may be selected from the group consisting of ammonium carbonate, sodium carbonate, potassium carbonate, ammonium bicarbonate, sodium bicarbonate, potassium bicarbonate and a combination thereof. Preferably, the precipitation of calcium comprises the addition of carbon dioxide and an alkali selected from the group consisting of ammonia, ammonium hydroxide, sodium hydroxide, potassium hydroxide, and a combination thereof, to the calcium-containing stream. The precipitation of calcium is preferably carried out at a pH of about 3 to about 11, a temperature of about 20° C. to about 95° C. and a time of about 5 min to about 48 hr.

After the calcium is precipitated, a sugar-containing stream may be obtained having a reduced concentration of calcium. This sugar-containing stream may be fermented to produce an alcohol, a sugar alcohol, an organic acid, or a combination thereof.

The neutralized, pretreated lignocellulosic feedstock preferably has a pH between about 4 and about 6.

The cellulase enzymes used in the enzymatic hydrolysis preferably comprise cellobiohydrolases (CBHs), endoglucanases (EGs) and f3-glucosidase.

In one embodiment of the invention, the enzymatic hydrolysis is carried out in the presence of a microorganism that converts glucose to at least one fermentation product.

BRIEF DESCRIPTION OF THE DRAWINGS

These and other features of the invention will become more apparent from the following description in which reference is made to the appended drawings wherein.

DETAILED DESCRIPTION OF THE INVENTION

Figure 1A:
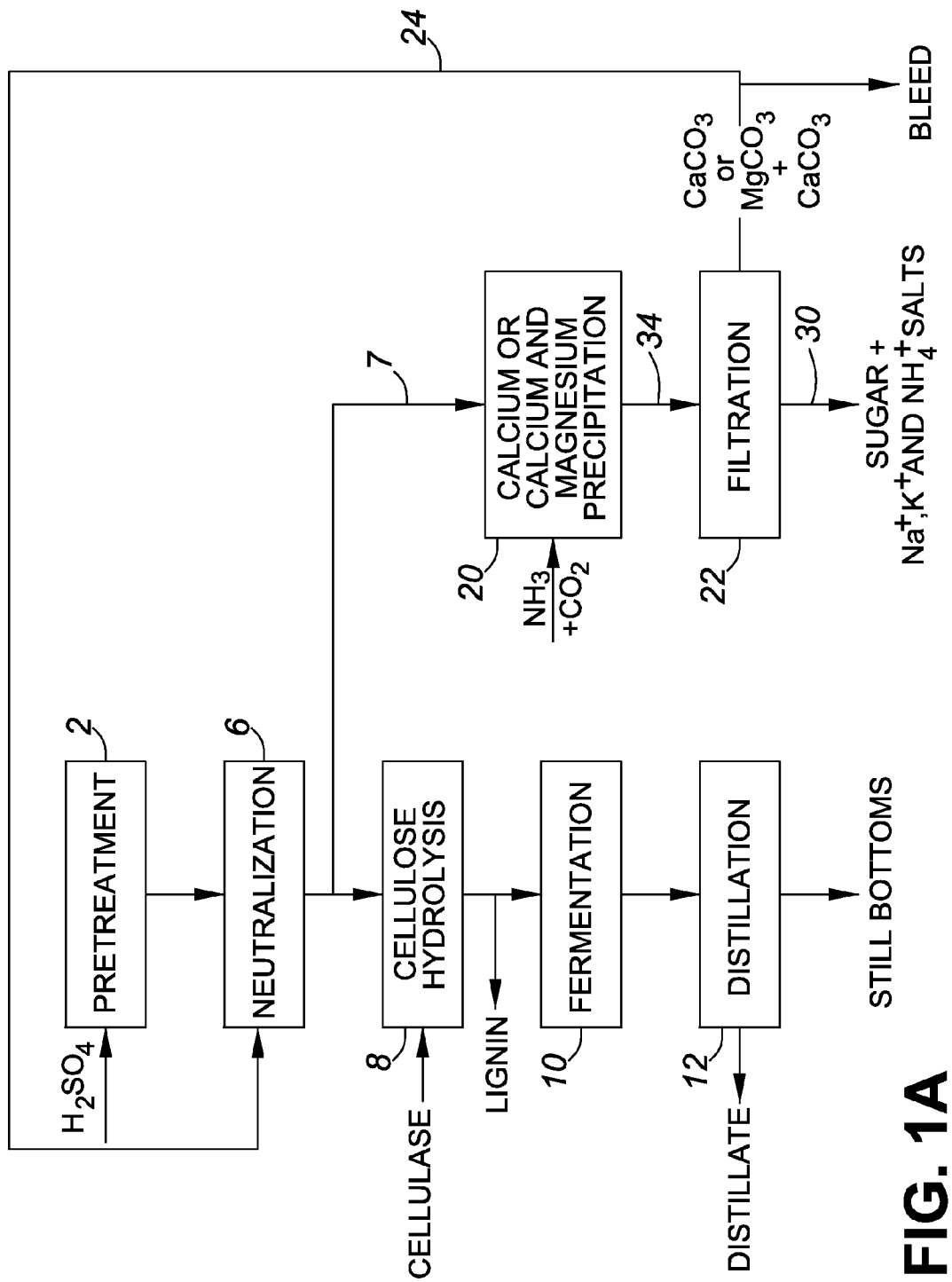
FIG. 1A depicts a process according to an embodiment of the invention in which a calcium-containing stream, which in this case is a sugar stream obtained, in turn, from a stream comprising a neutralized, pretreated feedstock is treated with carbon dioxide and alkali to precipitate calcium. This produces a calcium carbonate-containing stream (which additionally contains magnesium carbonate if magnesium is present in the feedstock) that is used to adjust the pH of an incoming acid pretreated feedstock to a pH that is amenable to cellulase enzymes (neutralization).

The following description is of an embodiment by way of example only and without limitation to the combination of features necessary for carrying the invention into effect.

Representative lignocellulosic feedstocks for use in the practice of the invention are (1) agricultural wastes such as corn stover, corn cobs, wheat straw, barley straw, oat straw, rice straw, canola straw, and soybean stover; (2) grasses such as switch grass, miscanthus, cord grass, and reed canary grass; and (3) forestry wastes such as aspen wood and sawdust. These feedstocks contain high concentrations of cellulose and hemicellulose that are the source of the sugar in the aqueous stream. These feedstocks contain calcium, and may additionally contain magnesium.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or any amount therebetween. Furthermore, the lignocellulosic feedstock comprises lignin in an amount greater than about 10%, more typically in an amount greater than about 15% (w/w). The lignocellulosic feedstock may also comprise small amounts of sucrose, fructose and starch.

The process of the present invention involves subjecting the lignocellulosic feedstock to an acid pretreatment. The acid pretreatment is intended to deliver a sufficient combination of mechanical and chemical action so as to disrupt the fiber structure of the lignocellulosic feedstock and increase the surface area of the feedstock to make it accessible to cellulase enzymes. Preferably, the acid pretreatment is performed so that nearly complete hydrolysis of the hemicellulose and only a small amount of conversion of cellulose to glucose occurs. The cellulose is hydrolyzed to glucose in a subsequent step that uses cellulase enzymes. Typically a dilute acid, at a concentration from about 0.02% (w/w) to about 5% (w/w), or any amount therebetween, (measured as the percentage weight of pure acid in the total weight of dry feedstock plus aqueous solution) is used for the pretreatment. Preferably, the acid is sulfuric acid.

The acid pretreatment is preferably carried out at a maximum temperature of about 160° C. to about 280° C. However, it should be understood that, in practice, there will be a time delay in the pretreatment process before the feedstock reaches this temperature range. Thus, the above temperatures correspond to those values reached after sufficient application of heat to reach a temperature within this range. The time that the feedstock is held at this temperature may be about 6 seconds to about 600 seconds. The pH of the pretreatment is preferably about 0.4 to about 3.0, or any pH range therebetween. For example, the pH of the pretreatment may be 0.4, 1.0, 1.5, 2.0, 2.5 or 3.0. Furthermore, the acid pretreatment may be carried out in more than one stage, although it is preferably performed in a single stage.

One method of performing acid pretreatment of the feedstock is steam explosion using the process conditions set out in U.S. Pat. No. 4,461,648 (Foody, which is herein incorporated by reference). Another method of pretreating the feedstock slurry involves continuous pretreatment, meaning that the lignocellulosic feedstock is pumped through a reactor continuously. Continuous acid pretreatment is familiar to those skilled in the art; see, for example, U.S. Pat. No. 5,536, 325 (Brink); WO 2006/128304 (Foody and Tolan); and U.S. Pat. No. 4,237,226 (Grethlein), which are each incorporated herein by reference. Additional techniques known in the art may be used as required such as the process disclosed in U.S. Pat. No. 4,556,430 (Converse et al.; which is incorporated herein by reference).

The acid pretreatment produces a composition comprising pretreated feedstock, which composition also contains calcium salts and optionally magnesium salts, and sugars produced by the hydrolysis of hemicellulose (xylose, glucose, arabinose, mannose, galactose or a combination thereof) and, to a lesser extent the hydrolysis of cellulose (in which case glucose is produced). The aqueous phase of the composition comprising the pretreated feedstock may also comprise the acid added during the pretreatment and any organic acids liberated during the pretreatment. When sulfuric acid is the acid utilized in the pretreatment, the composition comprising the pretreated feedstock additionally contains sulfate and/or bisulfate salts of calcium and possibly magnesium. These salts include calcium sulfate, magnesium sulfate and magnesium bisulfate. The composition comprising pretreated feedstock typically also contains potassium sulfate, potassium bisulfate, sodium sulfate and sodium bisulfate. The sulfate salts of the monovalent cations, potassium and sodium, are highly soluble in aqueous solution.

According to the invention, a recycle stream comprising calcium carbonate, calcium hydroxide (referred to herein as calcium carbonate- and calcium hydroxide-containing streams), or a combination thereof, is used to adjust the pH of the acid pretreated feedstock to a value amenable to cellulase enzymes. The calcium carbonate-containing stream may also comprise magnesium carbonate if magnesium is present in the feedstock. If a calcium hydroxide-containing stream is used for the pH adjustment, it is produced by calcination of the calcium carbonate, which process is discussed in more detail below. If magnesium carbonate is also present in the calcium carbonate-containing stream, magnesium hydroxide will be produced by the calcination as well. After pH adjustment, the cellulase enzymes hydrolyze the cellulose component of the feedstock to glucose.

According to the invention, the calcium carbonate-containing stream results from precipitation of calcium from a "calcium-containing stream". As used herein, this term refers to a stream that arises from any stage of the process, given that the calcium contained therein arises from the calcium present in the feedstock. If the stream contains insoluble solids, including, but not limited to lignin, it is preferable that they are removed prior to the precipitation step.

According to one embodiment of the invention, the calcium-containing stream, from which calcium is precipitated, is a sugar stream comprising xylose, glucose, or a combination thereof. The sugar stream may be obtained from the pretreated feedstock composition, for example, by washing the composition with an aqueous solution to produce a wash stream comprising the sugar, namely xylose, glucose, arabinose, mannose, galactose or a combination thereof, the calcium and optionally magnesium, the acid and other soluble components, and a solids stream comprising the remaining unhydrolyzed components of the feedstock. Alternatively, the composition comprising the pretreated feedstock is subjected to filtration, centrifugation, or other known processes for removing fiber solids or suspended solids. The aqueous sugar stream may then be concentrated, for example, by evaporation, with membranes, or the like. Any trace solids are typically removed by microfiltration.

Many lignocellulosic feedstocks contain hemicellulose with acetyl groups attached to xylan which are liberated as acetic acid during acid pretreatment or acid hydrolysis. Thus, the sugar stream will typically also comprise acetic acid. Additional organic acids that may be liberated during pretreatment, and that, therefore, may be present in the sugar stream, include galacturonic acid, formic acid, lactic acid, glucuronic acid or a combination thereof. The sugar stream may also contain other organic compounds, including but not limited to, furfural, hydroxymethyl furfural (HMF), dissolved lignin, and the like. The concentration of these compounds may be from about 0% to about 25% of the total solutes present in the aqueous stream, or from about 0% to about 10% of the total solutes present in the aqueous sugar stream.

The sugar stream may also be obtained after a stream comprising the pretreated lignocellulosic feedstock has been neutralized to a pH amenable to enzymatic hydrolysis, i.e., from a stream comprising neutralized, pretreated feedstock. This sugar stream may also contain the sugars liberated during the pretreatment step. According to this embodiment, the sugar stream may be obtained from the stream comprising neutralized, pretreated lignocellulosic feedstock by known solids-liquids separation techniques or by washing the neutralized, pretreated lignocellulosic feedstock. Examples of suitable solids-liquid separation techniques include centrifugation, microfiltration, plate and frame filtration, crossflow filtration, pressure filtration, vacuum filtration and the like.

The sugar stream may also be a stream comprising glucose resulting from cellulose hydrolysis with cellulase enzymes. The production of glucose resulting from enzymatic hydrolysis with cellulase enzymes is described in more detail below. However, it will be appreciated that this stream may additionally comprise sugars resulting from the pretreatment. Preferably, lignin and other insoluble solids are removed from this stream prior to precipitation using known solids-liquids separation techniques or the stream may be obtained by washing as described previously. Examples of suitable solids-liquid separation techniques include those set forth above.

The sugar stream may be obtained from other stages of the process not specifically described herein. It should also be appreciated that calcium may be precipitated from all or a portion of the sugar stream.

Another example of a calcium-containing stream from which calcium can be precipitated is a still bottoms stream. For example, if ethanol is the fermentation product of the process, it may be distilled to produce concentrated ethanol. After distillation, a "still bottoms stream" or "still bottoms" is produced. "Still bottoms stream" or "still bottoms" refers to the stream remaining after a distillation process, as is well known in the art.

When the calcium-containing stream from which calcium is precipitated is the still bottoms stream, the insoluble solids contained therein are typically removed prior to the precipitation to produce a clarified still bottoms stream. Examples of suitable solids-liquid separation techniques include centrifugation, microfiltration, plate and frame filtration, crossflow filtration, pressure filtration, vacuum filtration and the like. Furthermore, the still bottoms stream may be subjected to concentration, pH adjustment or dilution. It should also be appreciated that all or a portion of the still bottoms stream may be sent to the precipitation.

Furthermore, the still bottoms may be combined with the sugar stream from pretreatment to produce a combined still bottoms and sugar stream that is then fed to the neutralization. Alternatively, each stream may be fed separately to the neutralization.

Moreover, each of the sugar stream, the still bottoms stream and the combined sugar stream and still bottoms stream, or any other calcium-containing stream obtained from the process, may be subjected to further processing steps prior to calcium precipitation to produce the calcium carbonate-containing stream, including, but not limited to, ion exchange. Examples of such embodiments are described in more detail in turn below with reference to FIGS. 3-5.

In order to precipitate the calcium and produce the calcium carbonate-containing stream, the calcium-containing stream is treated with carbon dioxide, carbonate salts, bicarbonate salts, or a combination thereof. The carbonate salts may be selected from the group consisting of ammonium carbonate, sodium carbonate and potassium carbonate and the bicarbonate salts may be selected from the group consisting of ammonium bicarbonate, sodium bicarbonate and potassium bicarbonate, or a combination thereof. The precipitation may be conducted at a pH of between 3 and 11. For example, the pH may be 3, 3.5, 4.0, 4.5, 5.0, 5.5, 6.0, 6.5, 7.0, 7.5, 8.0, 8.5, 9.0, 9.5, 10, 10.5 or 11. Preferably, the calcium precipitation is conducted by the addition of carbon dioxide with alkali at a pH greater than about 5.0 to ensure sufficient solubility of carbon dioxide and low solubility of the carbonate salts. Examples of other suitable alkali besides carbonates include ammonium hydroxide, potassium hydroxide, sodium hydroxide, and ammonia alone or in combination with carbon dioxide. When a combination of alkali and carbon dioxide are used, they may be added separately to the sugar stream, or they may be combined to make a carbonate salt that is then added to the sugar stream. Furthermore, since the solubility of magnesium carbonate is very low, magnesium present in the calcium-containing stream can be removed by this precipitation step as well.

The calcium carbonate, and optionally magnesium carbonate, is removed from the aqueous solution of soluble salts by allowing the salt to precipitate and then separating the precipitate using known methods such as gravity separation, floatation, centrifugation, microfiltration, plate and frame filtration, crossflow filtration, pressure filtration, vacuum filtration and the like. The resulting calcium carbonate solids are optionally dried and then used to neutralize the pH of the pretreated lignocellulosic feedstock. Alternatively, the calcium carbonate may be provided in the form of an aqueous slurry. Thus, the calcium carbonate-containing stream can consist strictly of solids, can be a moist cake, or an aqueous slurry of calcium carbonate.

The precipitation of calcium carbonate, and optionally magnesium carbonate, may be carried out at any suitable temperature, for example, between about 20 and about 95° C., or any temperature range therebetween. A preferred temperature range is between about 40 and about 80° C., or any temperature range therebetween. For example, the temperature may be 20, 25, 30, 35, 40, 45, 50, 55, 60, 65, 70, 75, 80, 85, 90 or 95° C. These conditions are maintained for any suitable amount of time to allow the insoluble calcium precipitates to form, or longer as desired. The precipitation can be a batch or a continuous process. The calcium precipitates may form, for example, after about 5 to about 60 minutes, or any time range therebetween, more typically between about 10 and about 30 minutes, or any time range therebetween, although the total holding time in the vessel wherein the precipitation is carried out may be greater than this. For instance, the stream containing the insoluble calcium precipitates may be stored for a certain amount of time in the precipitation vessel prior to its addition to the stream comprising the pretreated feedstock. Moreover, separation of the calcium carbonate precipitate from the stream may be conducted in the precipitation vessel. Thus, the total holding time in the precipitation vessel may be greater than the amount of time required for precipitation to occur. Consequently, the total duration of the precipitation step may be from about 5 minutes to about 48 hours, or any time therebetween, or between about 15 minutes and about 24 hours, or any time therebetween. For example, the precipitation may be conducted for 5, 10, 15, 20, 25, 30, 35, 40, 45, 50, 55, or 60 minutes, or for 2, 4, 6, 8, 10, 12, 14, 16, 18, 20, 22, 24, 26, 28, 30, 32, 34, 36, 38, 40, 42, 44, 46 or 48 hours. The concentration of calcium salt in the calcium-containing stream fed to the precipitation step will depend on the calcium content of the feedstock, the form of the calcium salt and the operating conditions in processes prior to precipitation.

Furthermore, it should be appreciated that calcium may be added in the form of a salt like calcium carbonate or calcium sulfate, or lime may be added, to the neutralization at the start-up stage of the process. As will be appreciated by those of skill in the art, this is employed since, when the process is initiated, no calcium carbonate will yet be produced from the precipitation step. Also, calcium make-up may occur after a start-up stage. Thus, during the process, not all of the calcium is necessarily from calcium in the feedstock.

Moreover, not all of the calcium in the feedstock is necessarily recovered and reused since some of the calcium may be removed by a bleeding step.

Optionally, the stream comprising the pretreated feedstock is neutralized with a calcium hydroxide-containing stream produced by calcination of calcium carbonate in the calcium carbonate-containing stream. Typically this is conducted in a lime kiln. Calcination of calcium carbonate produces carbon dioxide and calcium oxide according to the following reaction:

$$CaCO_3 \xrightarrow{heat} CaO + CO_2.$$

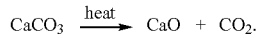

The calcium oxide can then be hydrated by the addition of water to form an aqueous solution of calcium hydroxide. It will be appreciated that calcium oxide can be added directly to the pretreated lignocellulosic feedstock composition, in which case it will be converted to calcium hydroxide upon addition, or the calcium oxide may be first hydrated in aqueous solution and then added to the pretreated feedstock. The calcination is typically conducted in a lime kiln at elevated temperatures to effect thermal decomposition of the calcium carbonate. It will be appreciated that calcination of calcium carbonate is a process that is well known to those of ordinary skill in the art.

The pH adjustment of the stream comprising pretreated feedstock involves adding sufficient calcium carbonate, calcium hydroxide, or a combination thereof, optionally with other alkali, to achieve a pH of about 3.0 to about 9, or any value therebetween. Preferably, the pH is greater than 3.5. In one embodiment of the invention, the pH is between about 3.5 and about 9, or between about 3.5 and about 6, or between about 4 and about 6. For example, the pH of the pretreated, neutralized feedstock may be 3.0, 3.5, 4.0, 4.5, 5.0, 5.5, 6.0, 6.5, 7.0, 7.5, 8.0, 8.5 or 9.0. The stream comprising calcium carbonate, calcium hydroxide, or a combination thereof, may be added in-line to the pretreated composition or directly to a hydrolysis vessel.

The pH adjustment may be conducted on a stream comprising not only the pretreated feedstock, but also sugars arising from pretreatment, namely xylose, glucose, arabinose, mannose, galactose, or a combination thereof. This occurs if the sugar and other soluble components resulting from pretreatment are not removed from the composition comprising pretreated feedstock. This stream may additionally contain the calcium and optionally also magnesium, the acid and other soluble components.

After pH adjustment of the stream comprising pretreated feedstock with the stream comprising calcium carbonate, calcium hydroxide, or a combination thereof, enzyme hydrolysis of the pretreated feedstock may then be conducted, for example, as described in WO 2005/099854 (Foody et al.) and pages 16-18 of WO 2006/063467 (Foody and Rahme), which are each incorporated herein by reference.

The enzymatic hydrolysis can be carried out with any type of cellulase enzymes, regardless of their source. Among the most widely studied, characterized and commercially produced cellulases are those obtained from fungi of the genera *Aspergillus*, *Humicola*, and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EG V and EGVI cellulases have been isolated from *Humicola insolens* (see Schulein et al., *Proceedings of the Second TRICEL Symposium on Trichoderma reesei Cellulases and Other Hydrolases*, Espoo 1993, P. Suominen and T. Reinikainen, Eds. Foundation for Biotechnical and Industrial Fermentation Research, Helsinki 8:109-116, which is incorporated herein by reference).

Following enzyme hydrolysis of the pretreated feedstock, any insoluble solids, including, but not limited to lignin, present in the resulting sugar stream may be removed using conventional solid-liquid separation techniques prior to any further processing. Alternatively, the solids and liquids in the sugar stream are both carried forward for further processing.

The hydrolysis may be a continuous process, with continuous feeding of pretreated feedstock slurry and withdrawal of hydrolysis product. Alternatively, the process may be a batch process.

Fermentation of glucose resulting from cellulose hydrolysis with cellulase enzymes may produce one or more of the fermentation products selected from an alcohol, a sugar alcohol, an organic acid and a combination thereof. Preferably, the alcohol is ethanol or butanol.

For ethanol production, fermentation is typically carried out with a *Saccharomyces* spp. yeast. Glucose and any other hexoses present in the sugar stream may be fermented to ethanol by wild-type *Saccharomyces cerevisiae*, although genetically modified yeasts may be employed as well. The ethanol may then be distilled to obtain a concentrated ethanol solution. The remaining still bottoms may then be subjected to a solids-liquid separation and the centrate recycled to the neutralization as described previously. However, most of the insoluble solids are typically removed after cellulose hydrolysis with cellulase enzymes.

Sugars liberated during pretreatment may also be present in the fermentation of glucose resulting from cellulose hydrolysis. This occurs if the aqueous portion of the pretreated feedstock composition, containing the sugars, xylose, glucose, arabinose, mannose, galactose, or a combination thereof, is carried through to the neutralization and cellulose hydrolysis. For example, if xylose is present in the fermentation, it may also be fermented to ethanol. Recombinant yeasts that can ferment xylose to ethanol are described in U.S. Pat. No. 5,789,210 (the contents of which are herein incorporated by reference). Furthermore, arabinose and xylose may be converted to ethanol by the yeasts described in Boles et al. (WO 2006/096130, which is incorporated herein by reference). Xylose may also be fermented to the sugar alcohol, xylitol, using a microorganism such as *Candida*.

The sugar stream obtained from the pretreated feedstock composition may be fermented as well. The sugar stream resulting from pretreatment will contain xylose, glucose, arabinose, mannose, galactose, or a combination thereof. This fermentation may be conducted before or after the calcium precipitation and may produce one or more of the fermentation products selected from an alcohol, a sugar alcohol, an organic acid and a combination thereof. The fermentation of xylose or both xylose and arabinose to ethanol may be conducted using the yeast set forth above. Xylose and other pentose sugars may be fermented to xylitol by a microorganism such as *Candida*. Prior to the fermentation, the sugar stream may be further processed to remove mineral acid and organic acids, or salts of these acids, preferably by anion exchange.

Non-limiting examples of other fermentation products included within the scope of the invention include butanol, sorbitol, 1,3-propanediol and 2,3-butanediol. Butanol is an especially preferred fermentation product. Other microorganisms that may be employed in the fermentations include wild-type or recombinant *Escherichia, Zymomonas, Candida, Pichia, Streptomyces, Bacillus, Lactobacillus* and *Clostridium*.

According to one embodiment of the invention, the cellulose hydrolysis with cellulase enzymes is conducted in the presence of a microorganism that converts glucose to one or more fermentation products. According to this embodiment, the cellulose hydrolysis to glucose is carried out concurrently with fermentation of glucose in a reactor vessel. By performing both reactions simultaneously, the microorganism consumes glucose by fermenting it to a fermentation product, such as ethanol, thereby reducing its concentration in the reactor which, in turn, decreases its inhibitory effect on the cellulase. Such a combined hydrolysis/fermentation reaction is known as Simultaneous Saccharification and Fermentation (SSF). When a simultaneous saccharification and fermentation (SSF) is conducted, the pH adjustment is conducted prior to the SSF. Preferably, the cellulose hydrolysis and fermentation are conducted in separate reactions.

Referring now to FIG. 1A, there is shown an embodiment of the invention in which the calcium-containing stream, from which calcium is precipitated, is a sugar stream obtained from a stream comprising a pretreated, neutralized feedstock. As shown in the figure, the lignocellulosic feedstock is first pretreated with acid in a pretreatment 2. Pretreatment 2 with acid hydrolyzes the hemicellulose, or a portion thereof, that is present in the lignocellulosic feedstock to the monomeric sugars xylose, glucose, arabinose, mannose, galactose or a combination thereof. Next, a neutralization 6 with alkali is carried out to adjust the pH of a stream comprising acid pretreated feedstock to a value that is amenable to cellulase enzymes, thereby producing the stream comprising the pretreated, neutralized feedstock. Sugar stream 7, containing calcium, is obtained, for example, by centrifugation (not shown) of the stream comprising the neutralized, pretreated lignocellulo sic feedstock and collecting the centrate, although the sugar stream 7 can be separated from the neutralized, pretreated feedstock by other means as discussed above. The calcium in sugar stream 7 is derived from calcium salts present in the lignocellulosic feedstock, which salts are carried through to aqueous sugar stream 7. This stream 7 may additionally contain magnesium salts that are native to the lignocellulosic feedstock.

Sugar stream 7 is next treated with carbon dioxide in a calcium or calcium and magnesium precipitation step 20 to produce calcium carbonate, and optionally also magnesium carbonate. In this embodiment, both ammonia and carbon dioxide are added to the sugar stream 7, which produces the calcium carbonate. Calcium carbonate is then removed from stream 34 by filtration 22, or other solid-liquid separation techniques, to produce a calcium carbonate-containing stream 24 containing calcium carbonate and optionally also magnesium carbonate and a stream 30 containing sugar from which calcium carbonate (and optionally additionally containing magnesium carbonate) is removed. It may be desirable to bleed a portion of the calcium carbonate prior to neutralization. Calcium carbonate that is removed by bleed can be disposed by landfill.

The calcium carbonate-containing stream (which optionally also contains magnesium carbonate) 24 is then recycled to a neutralization step 6 that is conducted to adjust the pH of the acid pretreated lignocellulosic feedstock to a value that is amenable to cellulase enzymes. After neutralization 6 of the pretreated lignocellulosic feedstock, cellulose hydrolysis 8 with cellulase enzymes is carried out.

The cellulose hydrolysis 8 produces an aqueous stream comprising glucose and unconverted solids that are primarily lignin. The glucose may be separated from the lignin solids and subjected to fermentation 10 to produce a solution containing ethanol, and the ethanol is then distilled in distillation 12 to produce a distillate containing concentrated ethanol and still bottoms. However, it will be appreciated that other fermentation products may be produced from the glucose as desired, as discussed previously.

Stream 30 contains sugars resulting from acid pretreatment of the hemicellulose component of the feedstock. The sugar in this stream may be fermented as well to produce an alcohol, a sugar alcohol, an organic acid, or a combination thereof. Preferably, the fermentation produces ethanol. The fermentation of xylose or both xylose and arabinose to ethanol may be conducted using genetically modified yeast set forth above. Xylose and other pentose sugars may alternatively be fermented to xylitol by a microorganism such as *Candida*. Prior to fermentation, stream 30 may be further processed to remove mineral acid and organic acids, or salts of these acids, preferably by anion exchange.

Figure 1B:
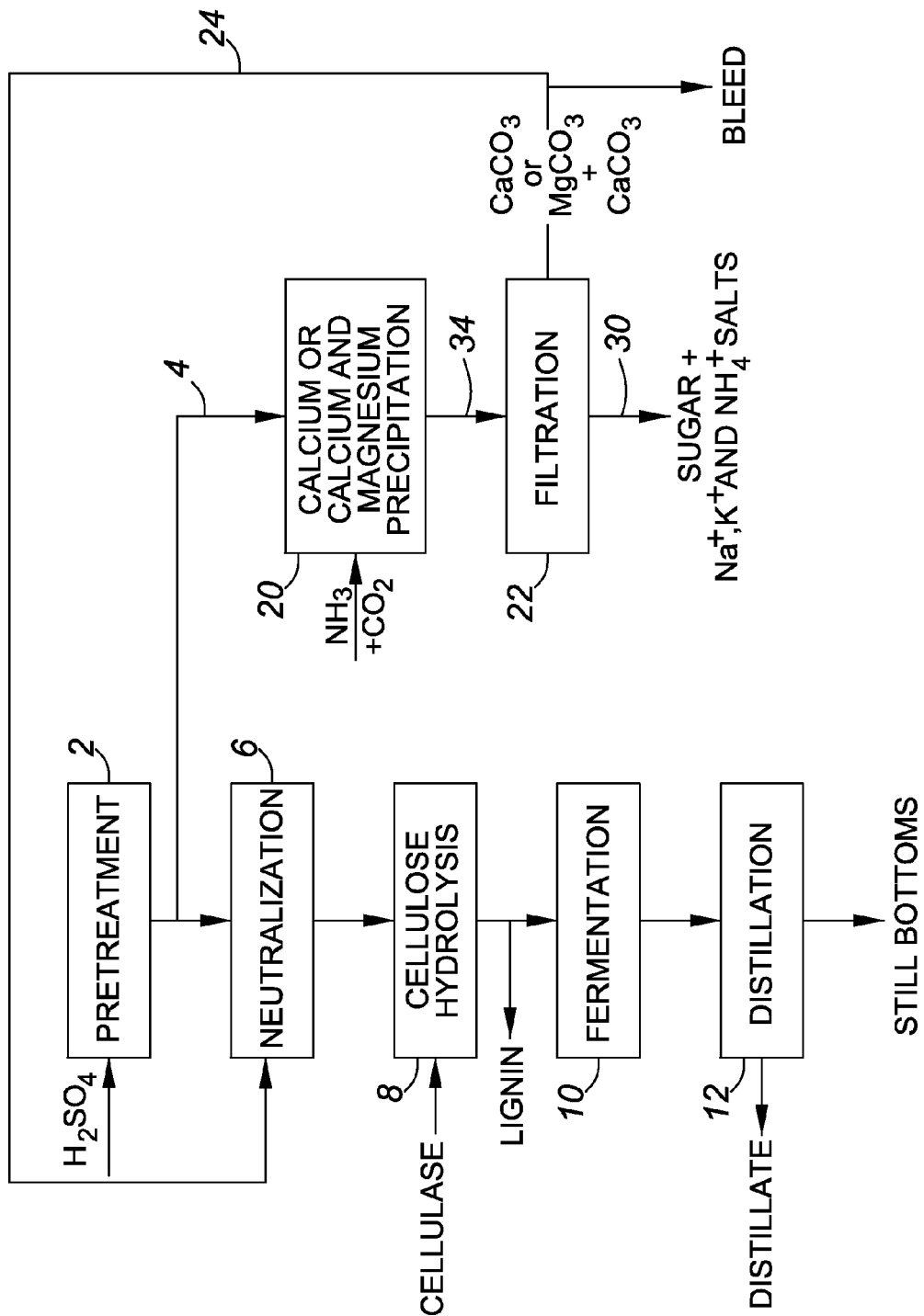
FIG. 1B is a process flow diagram that is similar to that of FIG. 1A except the calcium-containing stream that is fed to the calcium, or calcium and magnesium, precipitation step, is a sugar stream obtained from a stream comprising an acid pretreated lignocellulosic feedstock prior to neutralization.

According to another embodiment of the invention, the calcium-containing stream, from which calcium is precipitated, is a sugar stream 4 obtained from pretreatment. With reference to FIG. 1B, in which like reference numbers indicate identical or similar processing steps as in FIG. 1A, the lignocellulosic feedstock is first subjected to acid pretreatment 2, which produces xylose, glucose, arabinose, mannose, galactose or a combination thereof. Sugar stream 4, containing calcium from the lignocellulosic feedstock, is then obtained, for example, by centrifugation (not shown) of the pretreated lignocellulosic feedstock and collecting the centrate, although the sugar stream 4 can be separated from the pretreated feedstock by other means as discussed above. The sugar stream 4 is next treated, for example, with carbon dioxide and ammonia in a calcium or calcium and magnesium precipitation step 20 to produce calcium carbonate, and optionally also magnesium carbonate. After filtration 22, the resulting calcium carbonate-containing stream 24 is sent to neutralization 6 as described previously with reference to FIG. 1A.

Figure 1C:
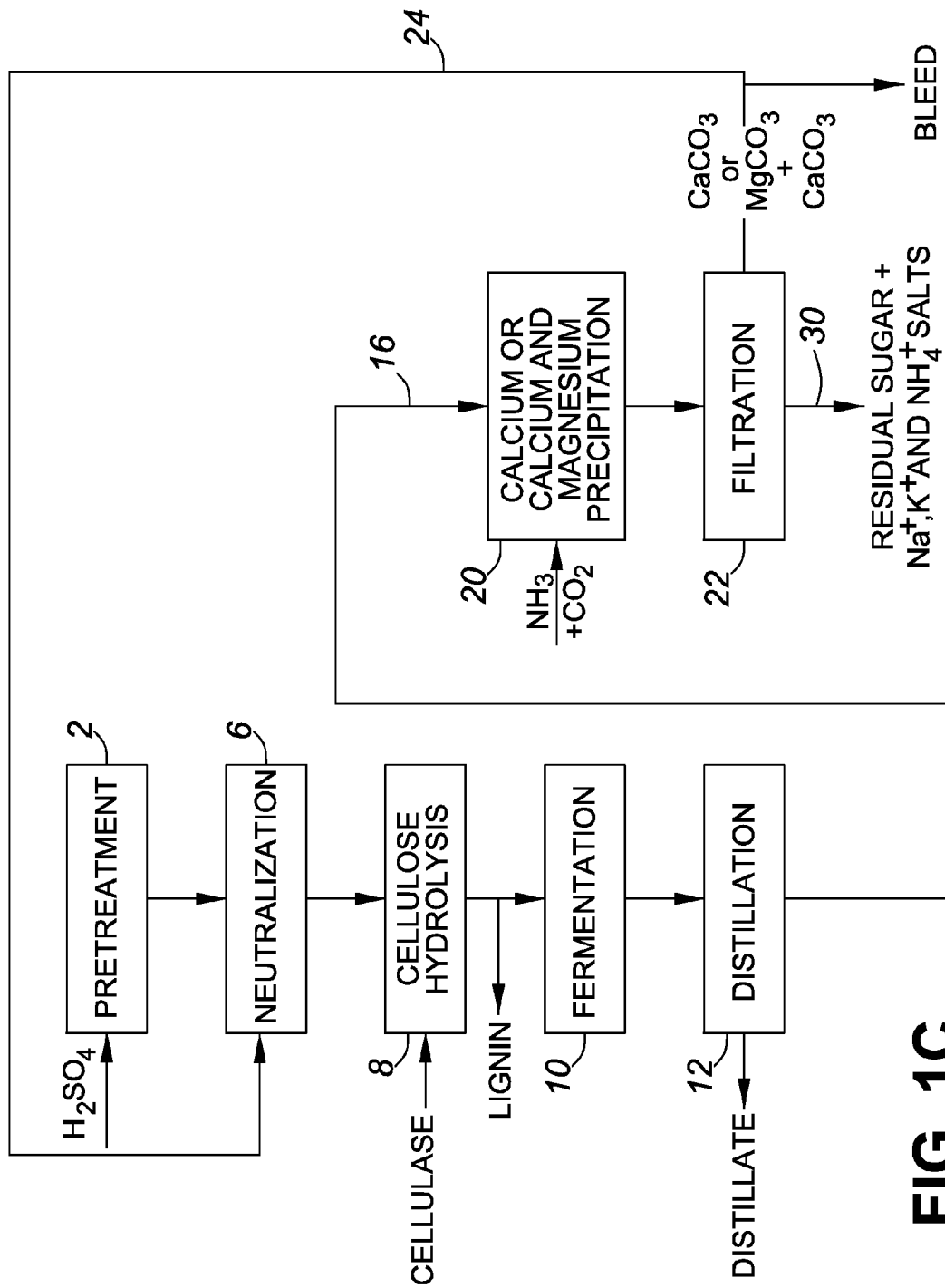
FIG. 1C is a process flow diagram that is similar to that of FIG. 1A except the calcium-containing stream that is fed to the calcium, or calcium and magnesium, precipitation step is a still bottoms stream.

In another embodiment of the invention, the entire aqueous stream containing the pretreated feedstock is sent to cellulose hydrolysis 8 without separating the fiber from the aqueous phase of the stream. Such an embodiment is depicted in FIG. 1C, in which like reference numbers indicate identical or similar processing steps as in FIG. 1A. In this case, both the pretreated feedstock resulting from pretreatment 2 and the aqueous portion containing sugars are subjected to neutralization 6 to adjust the pH of the pretreated feedstock prior to cellulose hydrolysis 8. The cellulose hydrolysis 8 produces a stream comprising glucose that may then be fermented in fermentation 10 to produce a fermentation product such as ethanol, followed by distillation 12. According to this embodiment, the stream sent to precipitation 20 is a still bottoms stream 16 remaining after distillation of the ethanol.

After cellulose hydrolysis 8, (FIG. 1C) both glucose, obtained from the cellulose hydrolysis, and xylose, glucose, arabinose, mannose, galactose, or a combination thereof, resulting from pretreatment, are typically present in the stream sent to fermentation 10. The sugars in this stream may be fermented to an alcohol, a sugar alcohol, an organic acid, or a combination thereof. Preferably, the alcohol is ethanol. In this case, the fermentation 10 may be performed with a recombinant *Saccharomyces* yeast that is engineered or obtained by artificial selection methods to ferment both hexose and pentose sugars to ethanol. However, the glucose may be fermented using wild-type *Saccharomyces* yeast. Xylose and other pentose sugars present in the stream may be fermented to xylitol, for example by a *Candida* species.

Figure 1D:
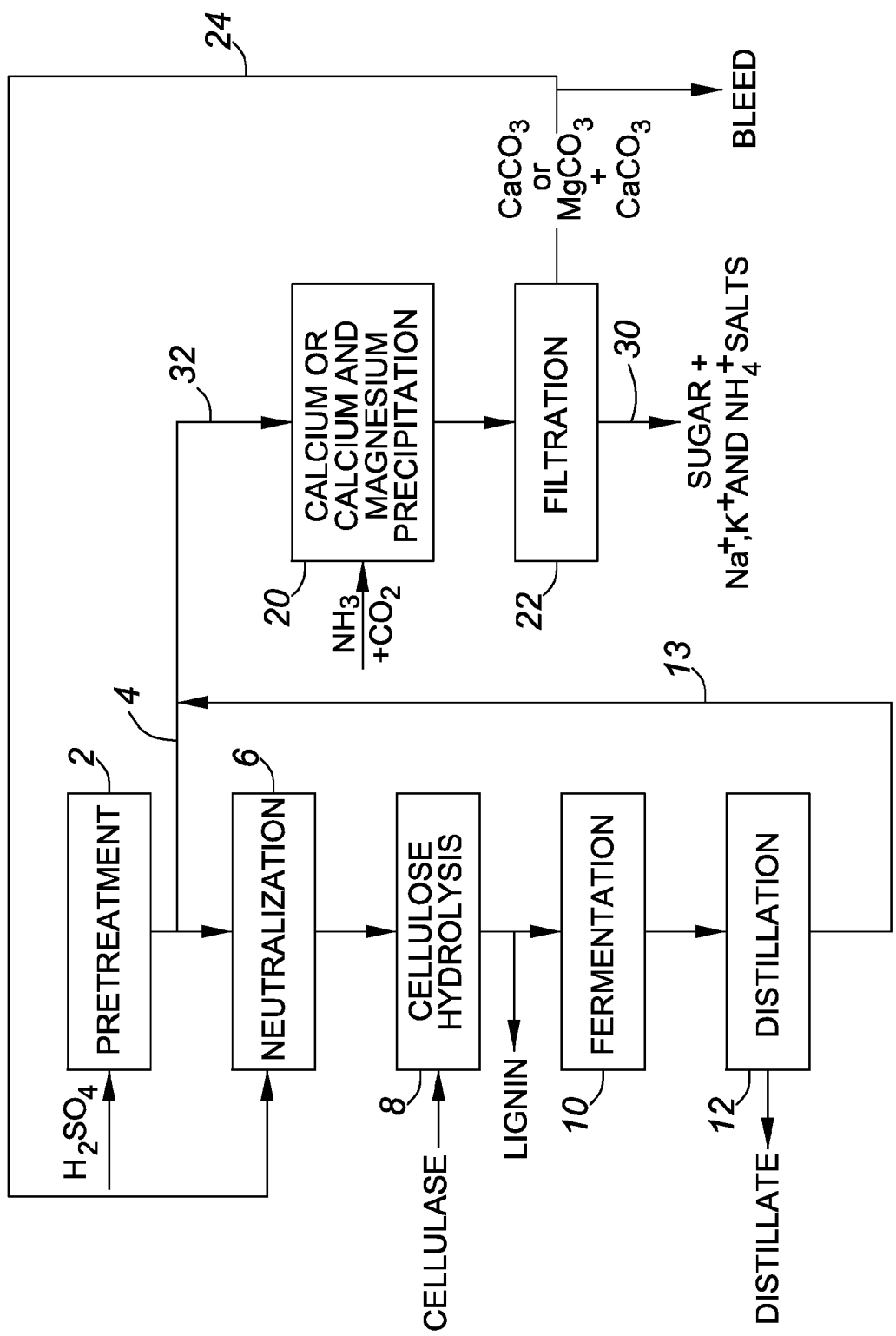
FIG. 1D is a process flow diagram that is similar to that of FIG. 1A except the calcium-containing stream that is fed to the calcium or calcium and magnesium precipitation step is a combined stream comprising a sugar stream from pretreatment and still bottoms.

Optionally, the sugar stream 4 separated from the pretreated feedstock is combined with a still bottoms stream remaining after distillation of the ethanol. Such an embodiment is depicted in FIG. 1D in which still bottoms stream 13 is combined with the sugar stream 4 obtained from pretreatment 2 to obtain a combined sugar stream and still bottoms stream 32. The combined sugar stream and still bottoms stream 32 is then sent to precipitation 20. Again, like reference numbers indicate identical or similar processing steps as in FIG. 1A.

According to this embodiment (FIG. 1D), the stream remaining after cellulose hydrolysis 8 will typically contain primarily glucose. The glucose may be fermented in fermentation 10 to an alcohol, a sugar alcohol, an organic acid, or a combination thereof. Without being limiting, the glucose may be fermented to ethanol using wild-type *Saccharomyces* yeast.

Stream 30 of FIG. 1D contains sugars resulting from acid pretreatment of the hemicellulose component of the feedstock. The sugar in stream 30 may be fermented as well to produce an alcohol, a sugar alcohol, an organic acid, or a combination thereof. Preferably, the fermentation produces ethanol. The fermentation of xylose or both xylose and arabinose to ethanol may be conducted using the genetically modified yeast set forth above. Xylose and other pentose sugars may alternatively be fermented to xylitol by a microorganism such as *Candida*. Prior to fermentation, stream 30 may be further processed to remove mineral acid and organic acids, or salts of these acids, preferably by anion exchange.

Figure 2:
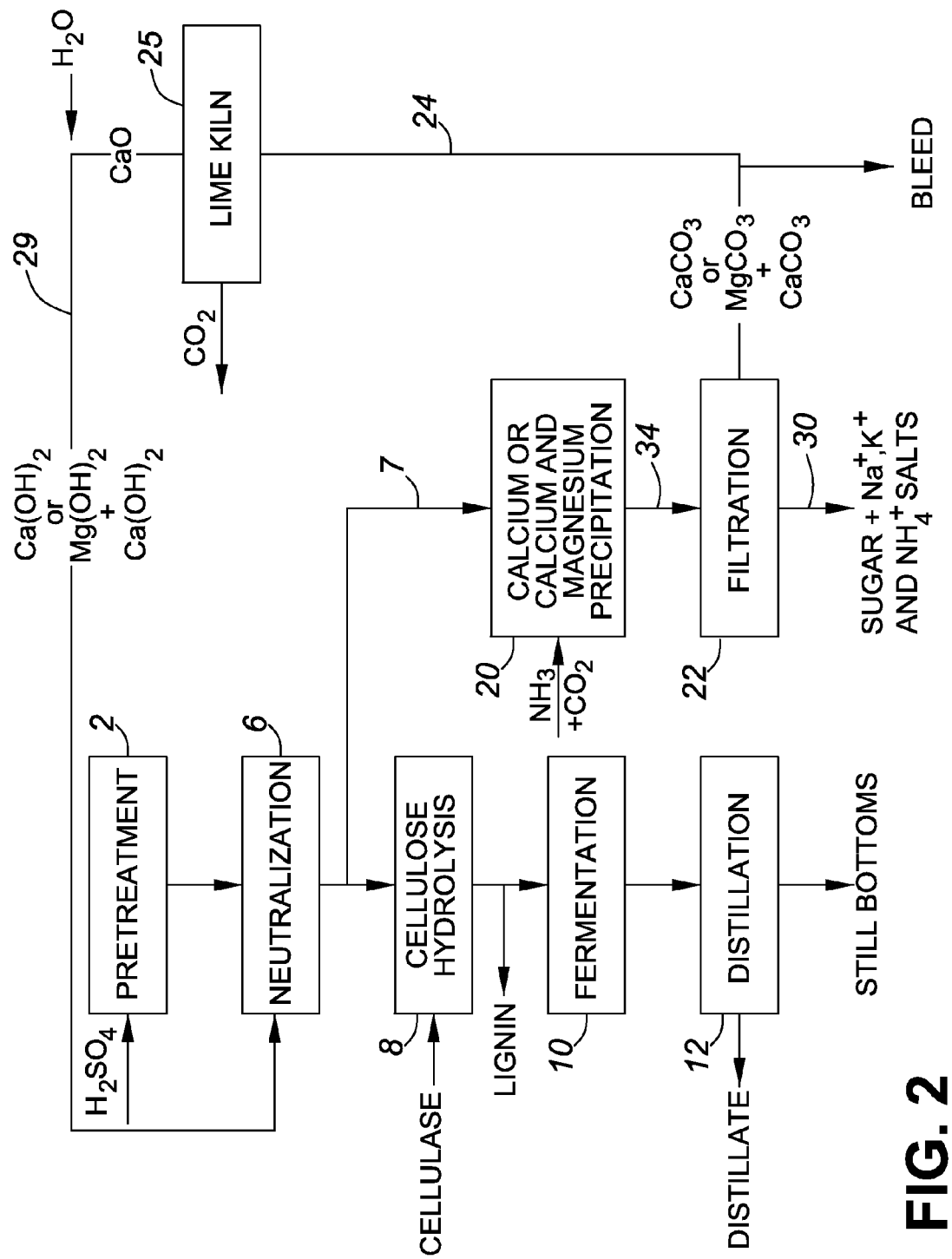
FIG. 2 is a process flow diagram that is similar to that of FIG. 1A except calcium hydroxide, which is obtained from the calcium carbonate by calcination, is recycled to the neutralization.

FIG. 2 depicts a process in which calcium hydroxide is used to adjust the pH of the pretreated feedstock. Like reference numbers indicate identical or similar processing steps as in FIG. 1A. FIG. 2 is similar to FIG. 1A, except that, according to this embodiment, the calcium carbonate-containing stream 24 is subjected to calcination in a lime kiln 25. Calcination of calcium carbonate in lime kiln 25 produces calcium oxide and carbon dioxide. The calcium oxide becomes hydrated by the addition of water to form an aqueous solution of calcium hydroxide 29. The resulting calcium hydroxide-containing stream 29 is then the stream used for the neutralization 6. If the calcium carbonate-containing stream 24 additionally contains magnesium carbonate, stream 29 will contain magnesium hydroxide.

Although, in FIG. 2, calcium, and optionally also magnesium, is precipitated from the sugar stream 7, the precipitation may be conducted on any stream containing calcium (i.e., the calcium-containing stream) that results from processing of the lignocellulosic feedstock to produce glucose, xylose, or a combination thereof, or any stream derived therefrom. For example, the calcium may be precipitated directly from a still bottoms stream, or from a combined sugar stream and still bottoms stream. (Similar to the embodiments depicted in FIGS. 1C and 1D). In another non-limiting example, the calcium-containing stream subjected to calcium precipitation, and optionally magnesium precipitation, is any one of a sugar stream, a still bottoms stream, and a combination thereof, which has been treated by ion exchange prior to the precipitation. An example of this latter non-limiting embodiment is discussed in more detail below. (See FIGS. 3-5).

Figure 3A:
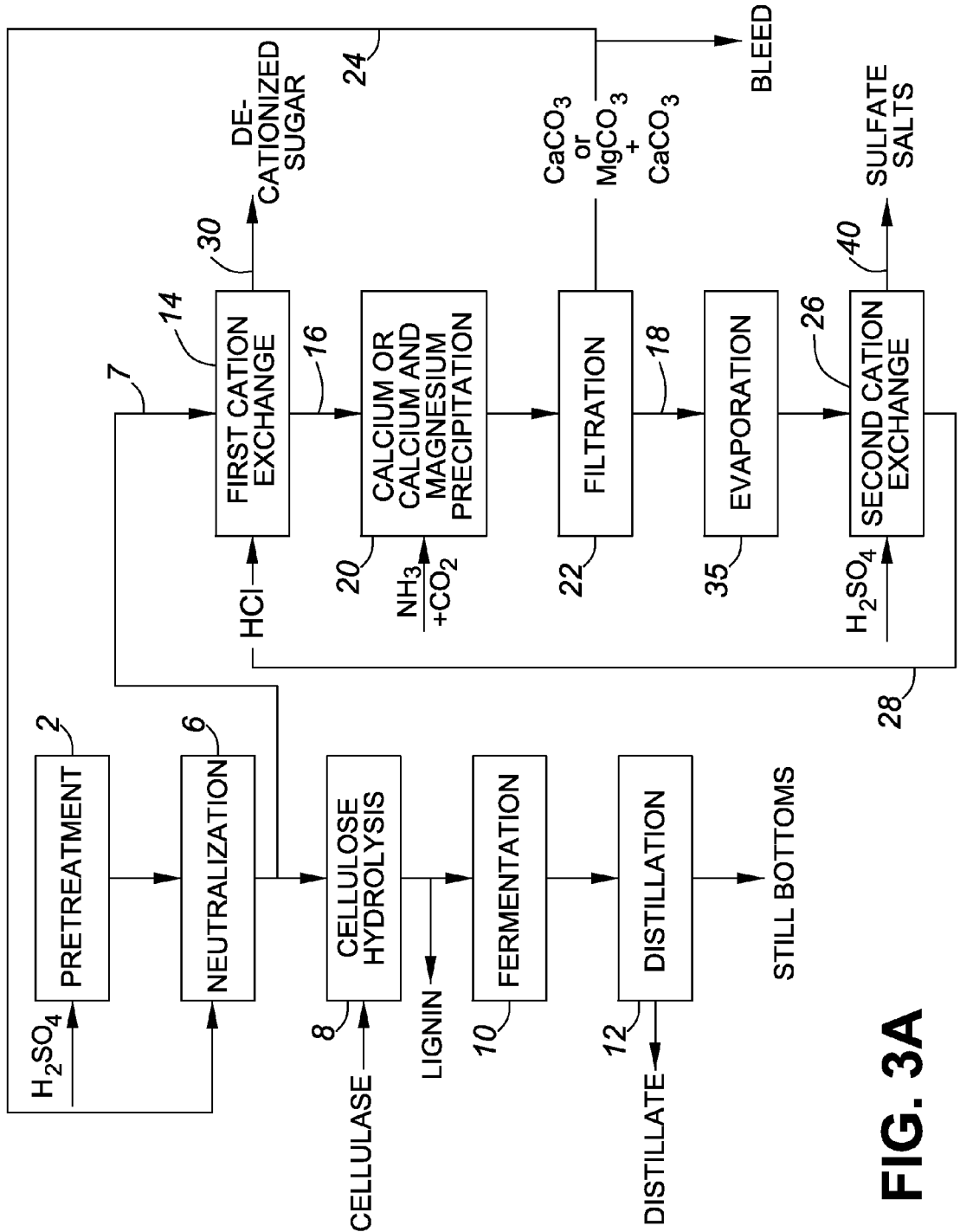
FIG. 3A depicts a process according to an embodiment of the invention in which a sugar stream obtained from a stream comprising a neutralized, pretreated lignocellulosic feedstock is passed through an ion exchange resin to reduce the concentration of calcium therein. The ion exchange resin is regenerated with hydrochloric acid to produce a calcium-containing salt stream. Carbon dioxide and alkali are then added to the salt stream to produce the calcium carbonate-containing stream (that may further comprise magnesium carbonate) that is recycled to the neutralization. The resulting clarified salt stream, which is substantially free of calcium, is sent to a second ion exchange resin. The second ion exchange resin is then regenerated with sulfuric acid, which produces sulfate salts.

Referring now to FIG. 3A, which depicts another non-limiting embodiment of the invention, the sugar stream 7 obtained from the neutralized, pretreated feedstock, and containing sugars resulting from pretreatment 2, is subjected to a first cation exchange 14 which removes cations therefrom to produce a de-cationized sugar stream 30. The first cation exchanger 14 is then regenerated. The salt stream 16 obtained upon regeneration of the first ion exchange 14 resin bed contains soluble calcium, which is then precipitated, for example, by the addition of carbon dioxide and ammonia in precipitation step 20. The reaction of the calcium with carbonate produces the calcium carbonate-containing stream 24 which, after filtration 22, is recycled to the neutralization step 6 performed before cellulose hydrolysis. According to this embodiment, after removal of calcium carbonate from the salt stream 16, the resulting clarified salt stream is evaporated 35 and then subjected to a second ion exchange operation 26 which utilizes, for example, sulfuric acid as a regenerant to produce the sulfate salts 40. These sulfate salts can subsequently be used as fertilizer or for other uses as desired.

By removing calcium from the salt stream 16, the subsequent formation of calcium sulfate in the second cation exchange resin bed 26 is avoided. As set forth in WO 2009/026707, if calcium is present in the feed stream to the second cation exchange, regeneration with sulfuric acid will produce calcium sulfate which precipitates in the resin bed. These precipitates are undesirable as they interfere with the ion exchange process and the flow of feed onto or through the column. Furthermore, they are difficult and expensive to remove from the resin bed.

Figure 3B:
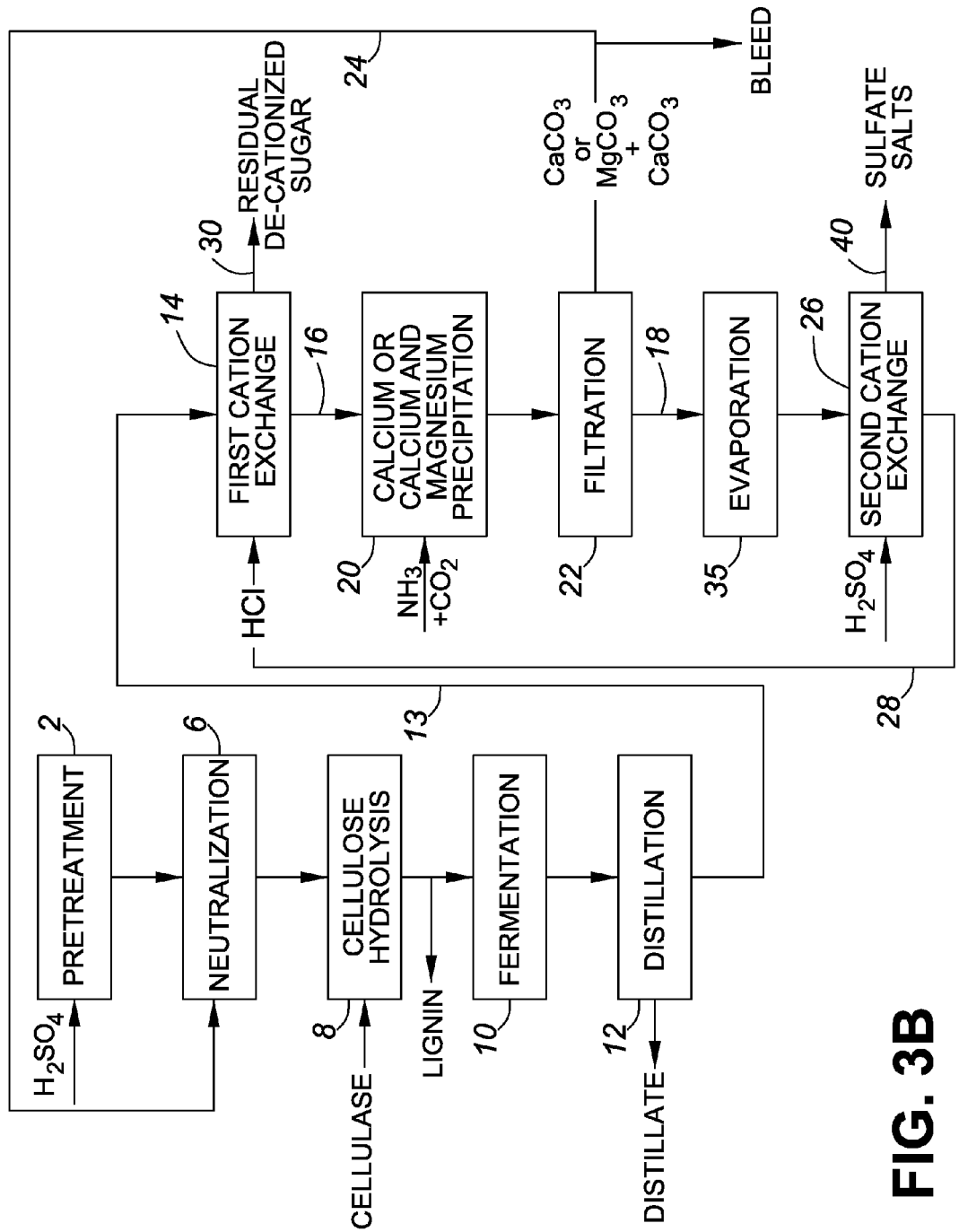
FIG. 3B is a process flow diagram that is similar to that of FIG. 3A except the stream that is fed to the first ion exchange resin is a still bottoms stream.
Figure 3C:
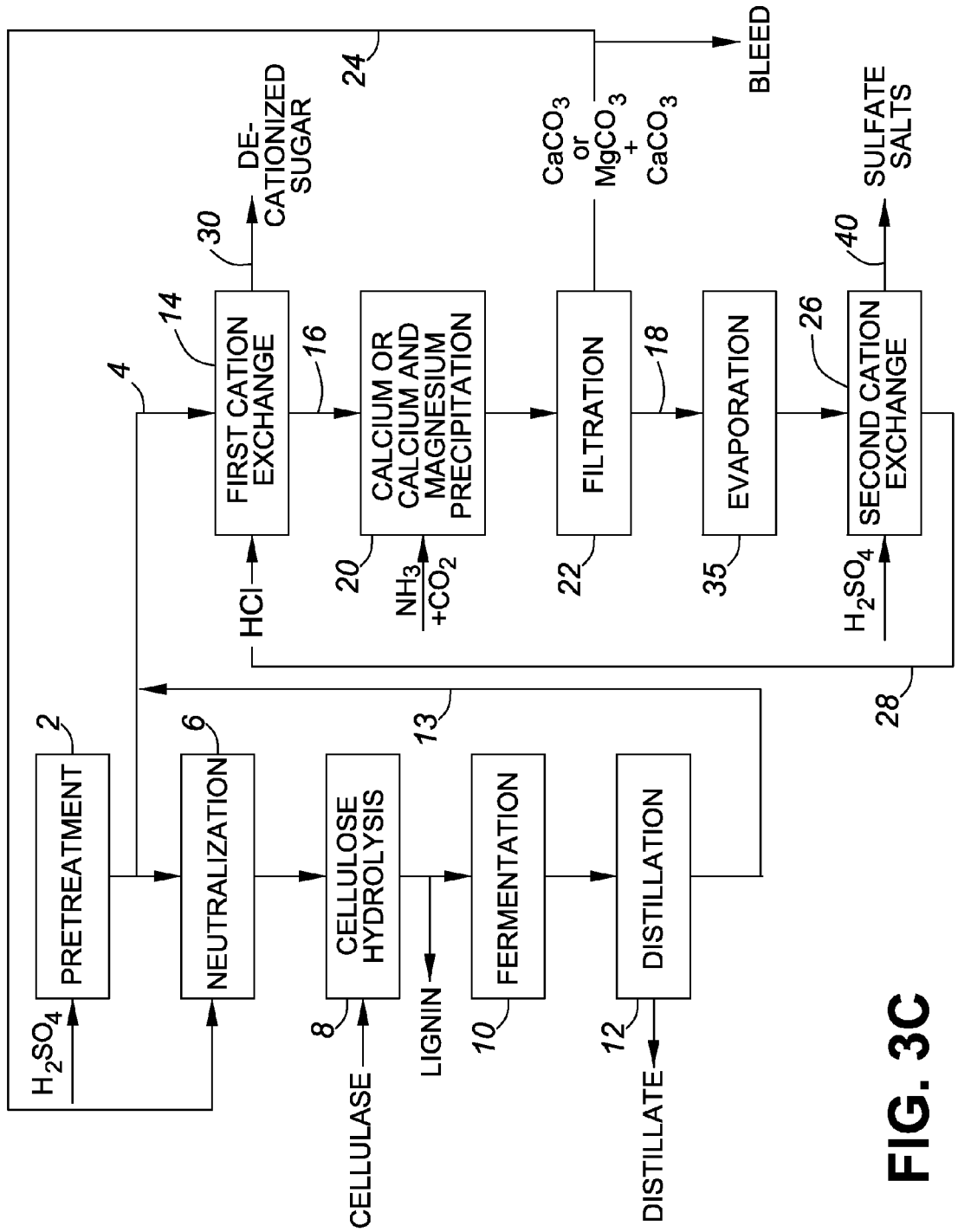
FIG. 3C is a process flow diagram that is similar to that of FIG. 3A except the stream that is fed to the first ion exchange resin is a combined stream comprising a sugar stream from pretreatment and still bottoms.

As depicted in FIG. 3A, the feed to the first cation exchange 14 is sugar stream 7 obtained from the stream comprising the neutralized, pretreated feedstock. However, the feed stream may result from other stages in the process. For example, as shown in FIG. 3B, the feed to the first cation exchange 14 may be a still bottoms stream obtained after distillation of ethanol. Alternatively, as illustrated in FIG. 3C, the feed may be a combined stream comprising a sugar stream 4 from pretreatment and still bottoms 13. Like reference numbers in FIGS. 3A, 3B and 3C depict identical or similar processing steps. The feed stream may also arise from other streams resulting from conversion of the lignocellulosic feedstock to glucose which have not been specifically described herein.

By the term "cation exchange resin", it is meant an insoluble solid matrix containing negatively charged sites that can interact with or bind to cations from a surrounding solution. This term is meant to include chelating resins which are described in more detail below. The cation exchange resin may be a strong or a weak acid resin, although strong acid cation exchange resins are preferred.

When the calcium-containing stream is fed to the first cation exchange resin, the resin becomes bound with cations in the stream by exchange with cations on the resin, while a stream, which may include sugar, inorganic acids and organic acids, or salts of these acids, elutes as a low-affinity stream. This may be achieved, for example, by feeding the calcium-containing stream to a cation exchange resin bed in the $H^+$ form, although it should be appreciated that other resin beds may be utilized, as will be described herein. Cation exchange resins typically bind both monovalent (e.g., sodium, potassium and ammonium ions) and divalent cations (calcium and magnesium ions). After a certain volume of the stream has been fed, the resin is regenerated. The feed stream may be fed until the breakthrough of monovalent cations, in which case the stream that passes through the resin bed contains no monovalent or divalent cations, or low levels of such cations. If the feed stream is fed until breakthrough of divalent cations, the stream that elutes from the resin prior to regeneration will contain monovalent cations. Any regenerant that desorbs the calcium and other cations bound to the cation exchange resin to make soluble salts of calcium and other cations may be utilized.

In one embodiment of the invention, the regeneration is carried out by the addition of acid to the cation exchange resin. In this embodiment, the anion of the acid reacts with the adsorbed cation(s) on the resin to produce soluble salts. Preferably, the acid is hydrochloric acid, which produces soluble calcium chloride upon regeneration, as well as the chloride salts of the other cations bound to the resin. It should be appreciated that if sulfuric acid is used as a regenerant for the first cation exchange it must be managed carefully since this acid can produce insoluble calcium sulfate salt that can precipitate within the resin bed.

The embodiments depicted in FIGS. 3A, 3B and 3C employ hydrochloric acid as a regenerant for the first cation exchange, although other regenerants may be used as desired. According to this embodiment, the first cation exchange 14 is in the $H^+$ form. As the calcium-containing stream 7 (FIG. 3A), 13 (FIG. 3B) or 4 (FIG. 3C) is fed to the first cation exchange 14, calcium and other cations of the sulfate salts, such as potassium, sodium and magnesium, replace $H^+$ on the resin, while a stream which may contain sugar, inorganic acids and/or organic acids, or salts of these acids, elutes as a low-affinity stream. The cations in the stream fed to the resin arise as sulfate salts from the addition of sulfuric acid in pretreatment.

The low-affinity stream that passes through the resin may be a de-cationized stream 30 with a reduced concentration of calcium, as well as substantially no potassium, sodium and magnesium ions. Alternatively, as discussed above, this low-affinity stream may contain monovalent cations if the feed to the resin is stopped after the breakthrough of divalent cations starts.

Once the resin bed is saturated with either divalent cations or both divalent and monovalent cations, it is regenerated back to the $H^+$ form by the addition of hydrochloric acid. If both monovalent and divalent cations adsorb onto the resin bed, the regeneration produces the salt stream 16 comprising calcium chloride and optionally also magnesium chloride if magnesium is present in the feedstock, as well as chloride salts of monovalent cations such as potassium chloride and sodium chloride. These salts result from the reaction of adsorbed cations with chloride ions, and excess hydrochloric acid. In contrast to calcium sulfate, the calcium chloride resulting from the regeneration is highly soluble in water and thus is not likely to precipitate within the resin bed. The excess hydrochloric acid may be recovered by an acid recovery unit (not shown) and then recycled back to the cation exchanger for use as a regenerant.

The de-cationized stream 30 comprising compounds with low affinity for the resin may be further processed. For example, if stream 30 contains sugars or acids, it may be processed to remove acids and then subjected to fermentation to produce ethanol or other fermentation products, as set forth previously with reference to FIGS. 1A-C. Although a de-cationized stream 30 is shown in the drawings, this sugar-containing stream may also contain monovalent cations, as discussed previously. These monovalent cations may be present in the stream during fermentation.

The concentration of hydrochloric acid used to regenerate the cation exchange resin bed may be about 1% to about 20%, or any concentration range therebetween. If the regenerant concentration is less than 5%, then excess water will likely be required, and regeneration times will likely be too long for practical consideration. The concentration of chloride salts will be too low for efficient processing. However, if the HCl concentration is too high, there is the risk of osmotic shock to the resin when water is added back to the system. The regenerant concentration is preferably about 5% to about 8%, or any concentration range therebetween.

According to any of the aforementioned embodiments of the present invention, the regenerant can be fed to the resin bed in the same direction as the aqueous feed, which is known as "co-current regeneration". Alternatively, the regenerant may be counter-current, meaning that the regenerant feed is in the opposite direction to the aqueous feed. Following regeneration, the column(s) are optionally rinsed with water or other aqueous streams prior to resuming feed of the aqueous stream.

The resin bed used in any of the previously-described embodiments may be an elongate vertical column filled with the resin. Alternatively, a short column with a small height-to-diameter ratio may be employed. Such columns are utilized in RECOFLO® ion exchangers that are commercially available from Eco-Tec. As would be apparent to one of skill in the art, the volume of the resin bed is typically chosen based on the flow rate and the concentration of salts and acid in the calcium-containing stream. The sizing of resin beds may be carried out by combining the data from laboratory, or other experiments, on the feed stream with design principles that are familiar to those skilled in the art.

The cation exchange resin bed may include a single column or multiple columns. If multiple columns are employed, they may be arranged in parallel and/or in series.

As will be appreciated by those of skill in the art, the operating conditions of the cation exchange operation may be adjusted as desired. For example, the temperature at which the cation exchange is conducted may range from ambient temperature to about 90° C. Elevated temperatures may be achieved by placing a heating jacket around the ion exchange unit and monitoring the temperature. The average flow rate of the feed may be between about 0.5 and about 20 L of feed/L resin/hr, or any value therebetween.

The cation exchange operation may be carried out using a Simulated Moving Bed (SMB) system. By the term "SMB system", it is meant any continuous chromatographic technique which simulates a flow of a liquid mobile phase moving countercurrent to a flow of a solid stationary phase, i.e., the SMB system simulates movement of the resin bed in a direction opposite to that of the liquid flow. Typically, an SMB system comprises multiple resin beds connected in a closed or open circuit with two or more inlet and two or more outlet streams. The simulated movement may be carried out by periodically shifting four or more flow locations by some fraction of the total bed. A description of the operation of an SMB system is provided in WO 2006/007691 (Foody and Tolan), to which the reader is directed for reference and which is incorporated herein by reference. Improved SMB ("ISMB") systems (available for example from Eurodia Industrie S. A., Wissous, France; Applexion S. A., Epone, France; or Amalgamated Research Inc., Twin Falls, Id.) may also be used in the practice of the invention.

One type of continuous ion exchange separation system that may be used in accordance with the invention is ISEP®, which is available through Calgon Carbon Corporation. In a typical ISEP®, a carousel arrangement of moving columns of small ion exchange beds slowly rotates between stationary ports. The carousel, rotating under the distribution ports, moves the columns through the normal ion exchange sequence which involves adsorption, backwash, regeneration and rinse.

Following regeneration, the cation exchange bed is optionally rinsed with water or other aqueous streams prior to resuming feed of the aqueous sugar stream. Rinsing may also be carried out following feed of the aqueous sugar stream to the resin bed and prior to regeneration. In either case, the rinsing step is preferably conducted by applying about 0.5 to about 2.0 resin bed volumes of water to the resin bed.

In each of the embodiments described in FIGS. 3A, 3B and 3C, both ammonia and carbon dioxide are added to the salt stream 16, which produces the calcium carbonate. However, as discussed above, this may alternatively involve the addition of carbonate salts, bicarbonate salts, carbon dioxide, or a combination thereof, to produce calcium carbonate. Calcium carbonate is then removed from the salt stream by filtration 22, or other solid-liquid separation techniques, to produce stream 24 comprising calcium carbonate. This stream is then recycled to the neutralization step 6 to adjust the pH of the pretreated lignocellulosic feedstock prior to enzymatic hydrolysis with cellulase enzymes.

The neutralization may also be conducted with calcium hydroxide derived from calcium carbonate in the calcium carbonate-containing stream 24 as set forth above with reference to FIG. 2.

After removal and recycle of the insoluble calcium precipitate from the salt stream, the salts of the monovalent cations remaining in the resulting clarified salt stream may be converted to their sulfate salts. As noted previously, this may be carried out by using cation ion exchange with sulfuric acid as a regenerant. When a cation exchange resin is employed to obtain the sulfate salts, the resin is typically saturated with cations of the soluble salts present in the clarified salt stream by exchanging with cations on the resin. Compounds with low-affinity for the resin pass through the resin bed. When the resin is then regenerated with sulfuric acid, it reacts with the cations adsorbed on the resin to produce a salt stream comprising sulfate salts.

Referring again to FIGS. 3A, 3B and 3C, the clarified salt stream 18 resulting from the filtration 22 is evaporated 35 prior to being fed to the second cation exchange operation 26. According to these embodiments, the second cation exchange operation 26 contains a strong acid cation exchange in the $H^+$ form. Thus, as the salt stream is fed to the second cation exchange 26, the cations of the soluble salts displace $H^+$ on the resin bed. Hydrochloric acid formed from the chlorides and the $H^+$ exits the resin bed in stream 28. After the resin is saturated with the cations, it is regenerated with sulfuric acid, which converts the resin back to the $H^+$ form and produces the sulfate salt product stream 40 comprising ammonium sulfate, sodium sulfate and potassium sulfate. The stream 40 will be free of calcium sulfate salt since this cation is not present in the solution fed to the ion exchange. If the calcium-containing stream 7 (FIG. 3C) that is obtained from the neutralized, pretreated feedstock results from neutralization with ammonia or ammonium hydroxide, the sulfate salt stream 40 will contain additional ammonium sulfate.

Moreover, if the feed to the first cation exchange 14 (e.g., calcium-containing streams 7, 13 or 4 in FIGS. 3A, 3B and 3C, respectively) is conducted until breakthrough of divalent cations, monovalent cations will be in the low affinity stream that passes through the resin of the first cation exchange. In this case, the monovalent cations that adsorb to the second cation exchange will be cations of salts added during precipitation of the calcium. For example, if ammonia is added during precipitation of calcium, ammonium ions will adsorb to the resin of the second cation exchange and ammonium sulfate will be produced upon regeneration with sulfuric acid.

Although the above-described embodiment employs a cation exchanger 26, anion exchange may be employed at this point to obtain the product stream comprising sulfate salts, for example as described by U.S. Pat. No. 4,707,347 (Vajne), which is incorporated herein by reference.

As in the first cation exchanger 14, the regenerant can be fed co-current or counter-current to the direction of the clarified salt stream feed. The cation exchange resin is typically a strong acid cation exchange resin. By a strong acid cation exchange resin, it is meant a resin with a polymeric structure comprising a strong acid functional group. A common strong acid functional group found in strong acid cation exchange resins is a sulfonate group, although other groups may be employed as desired.

Similar to the first cation exchange operation, the cation exchanger 26 used to produce the sulfate salts may be an elongate vertical column filled with resin or a short column with a small height-to-diameter ratio. The cation exchange operation may comprise multiple beds arranged in parallel and/or in series. The volume of the resin bed is typically chosen based on the flow rate and the concentration of salts and acid in the sugar stream. Furthermore, the sizing of resin beds may be carried out by combining the data from experiments on the aqueous sugar stream with design principles that are familiar to those skilled in the art. The cation exchange operation may be an SMB or an ISMB operation as described above. Following regeneration of the resin bed, it is optionally rinsed with water or other aqueous streams prior to resuming feed of the aqueous sugar stream. Rinsing may also be carried out following feed of the aqueous sugar stream and prior to regeneration. This is preferably conducted by applying about 0.5 to about 2.0 resin bed volumes of water to the resin bed.

The resin bed of the cation exchanger 14 or 26 may be regenerated with the excess acid in the regenerated streams. In one embodiment of the invention, excess acid present in the regenerated stream from the first cation exchanger is re-used to regenerate this resin bed. In this embodiment, the acid is recovered from other compounds present in the stream. In a further embodiment of the invention, the excess acid present in the regenerant from the second ion exchanger is recovered from the sulfate salt stream and fed back to the second cation exchanger.

Examples of methods that may be employed to recover the excess acid in the salt stream are distillation and acid retardation. Acid retardation is a particularly preferred method for recovering acids and employs strongly basic anion exchange resins to bind or adsorb mineral acid. Organic acids, salts and other compounds which have low affinity for the resin pass through the bed, while the adsorbed acid elutes later after addition of a regenerant, which is typically water. Acid retardation is known and is described in Hatch and Dillon (Industrial & Engineering Chemistry Process Design and Development, 1963, 2(4):253-263) and Anderson et al. (Industrial and Engineering Chemistry, 1955, 47(8):1620-1624) which are each incorporated herein by reference. Evaporation or distillation can be utilized when the acids to be recovered have a high volatility, such as HCl.

Figure 4:
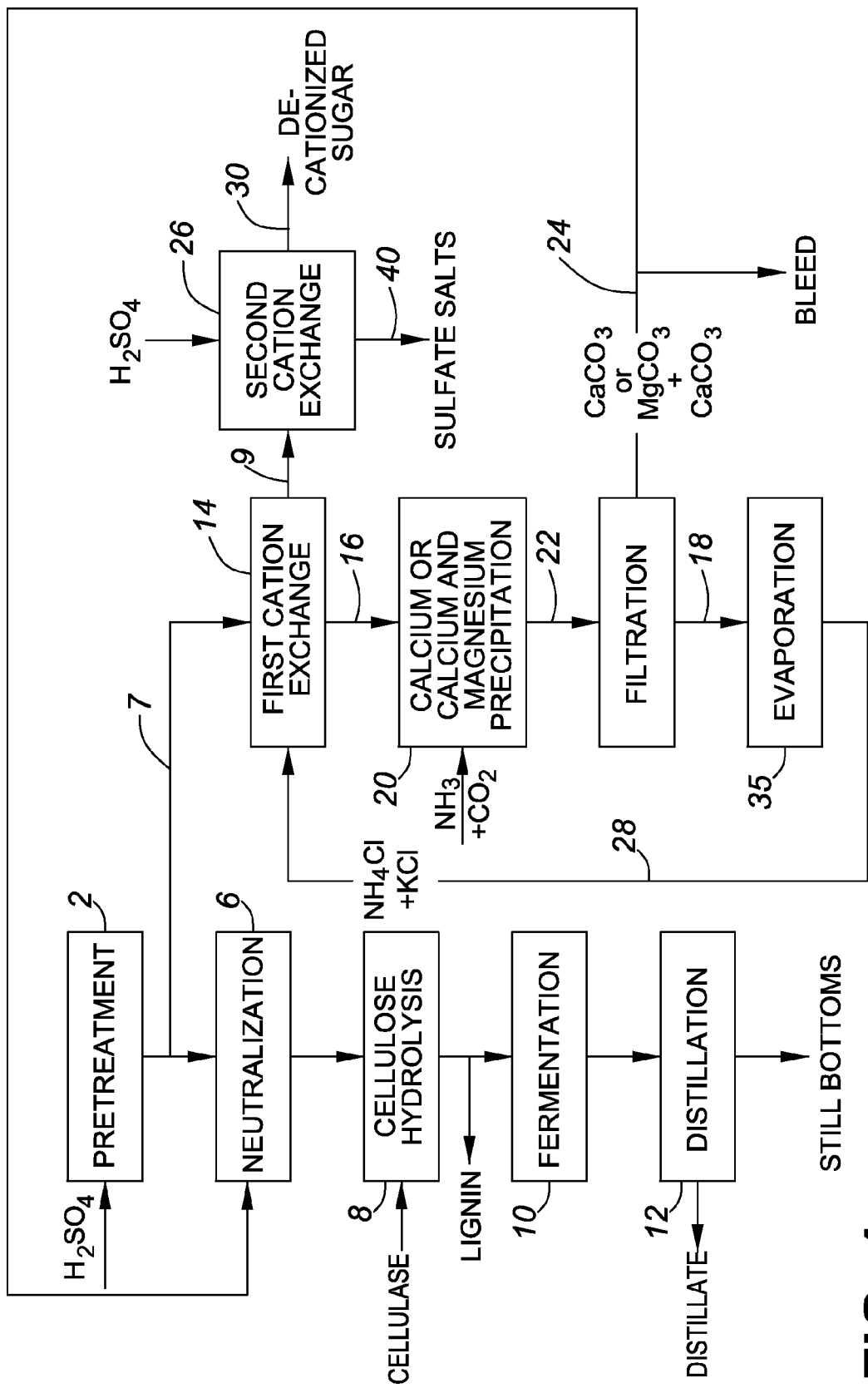
FIG. 4 is a process flow diagram for recycling a calcium carbonate-containing stream to the neutralization according to another embodiment of the invention. This embodiment utilizes a two-stage cation exchange process which produces a sugar stream comprising sulfate salts. The first stage of the cation exchange is conducted on a sugar stream obtained from a stream comprising a pretreated, neutralized feedstock and employs NaCl, $NH_4Cl$ and KCl as the regenerant. Carbon dioxide and alkali are added to the salt stream obtained upon regeneration of the first stage cation exchanger. This produces the calcium carbonate-containing stream that is recycled to the neutralization. The second stage cation exchange is conducted on a sugar stream obtained from the first cation exchange. Sulfuric acid is used to regenerate the resin bed of the second cation exchanger, which produces the stream comprising the sulfate salts.

FIG. 4 shows an alternative embodiment of the invention. Similar to the above-described processes (FIGS. 3A, 3B and 3C), this embodiment employs a two-stage cation exchange process. However, in this case, the first cation exchanger is regenerated with soluble salts such as sodium, potassium and ammonium salts rather than acid as described previously.

As shown in FIG. 4, a sugar stream 7 comprising ammonium sulfate, potassium sulfate, sodium sulfate, calcium sulfate and magnesium sulfate is fed to a first cation exchanger 14 having a resin bed saturated or nearly saturated with ammonium and potassium ions. In this embodiment a low affinity sugar stream 9 comprising sugar, ammonium sulfate, sodium sulfate and potassium sulfate is obtained from the first cation exchanger 14.

After the resin bed of the first cation exchanger 14 is saturated with cations, it is regenerated by the addition of sodium chloride, ammonium chloride and potassium chloride salts in stream 28. This produces a stream 16 comprising the calcium salt, calcium chloride, as well as ammonium chloride, potassium chloride, sodium chloride and magnesium chloride, and converts the resin back to the $NH_4^+/K^+/Na^+$ form. Stream 16 is then treated with carbon dioxide and ammonia, or other alkali, such as carbonate salts or bicarbonates salts, in a calcium precipitation step 20, as described previously, to precipitate calcium and magnesium carbonate salts, which are then removed from solution by filtration 22. A stream 24 containing calcium carbonate and magnesium carbonate resulting from the filtration 22 is then recycled to neutralization 6. Clarified salt stream 18 containing the remaining ammonium chloride, sodium chloride and potassium chloride salts is evaporated 35 and then recycled to the first cation exchanger 14 to regenerate the resin bed. Evaporation 35 of stream 18 preferably is conducted prior to its re-circulation to the first cation exchanger 14 to offset any dilution of the salts in precipitation or filtration.

When potassium chloride, ammonium chloride and sodium chloride are used to regenerate the first cation exchange resin bed, any concentration suitable for regeneration may be employed. For example, the concentration of these salts may be between about 3% and about 15%, or any concentration range therebetween. Although the use of $K^+/NH_4^+/Na^+$ salts are described, it should be understood that other salts, or mixtures of salts, may be employed as desired to regenerate the resin bed.

The low affinity sugar stream 9 obtained from the first cation exchanger 14 contains reduced amounts of calcium and comprises sugar, ammonium sulfate, sodium sulfate and potassium sulfate. This stream 9 is then fed to a second cation exchanger 26 to obtain sulfate salts of the monovalent cations. As stream 9 is fed to the second cation exchanger 26, the ammonium, sodium and potassium ions of the sulfate salts bind to the resin, while sugar and acid 30 pass through the resin bed. The second cation exchanger 26 is then regenerated with sulfuric acid to obtain the product stream comprising ammonium, sodium and potassium sulfate salts 40.

Stream 30 may be further processed to remove mineral acid and organic acids and then fermented as described previously with reference to FIG. 1A.

Figure 5:
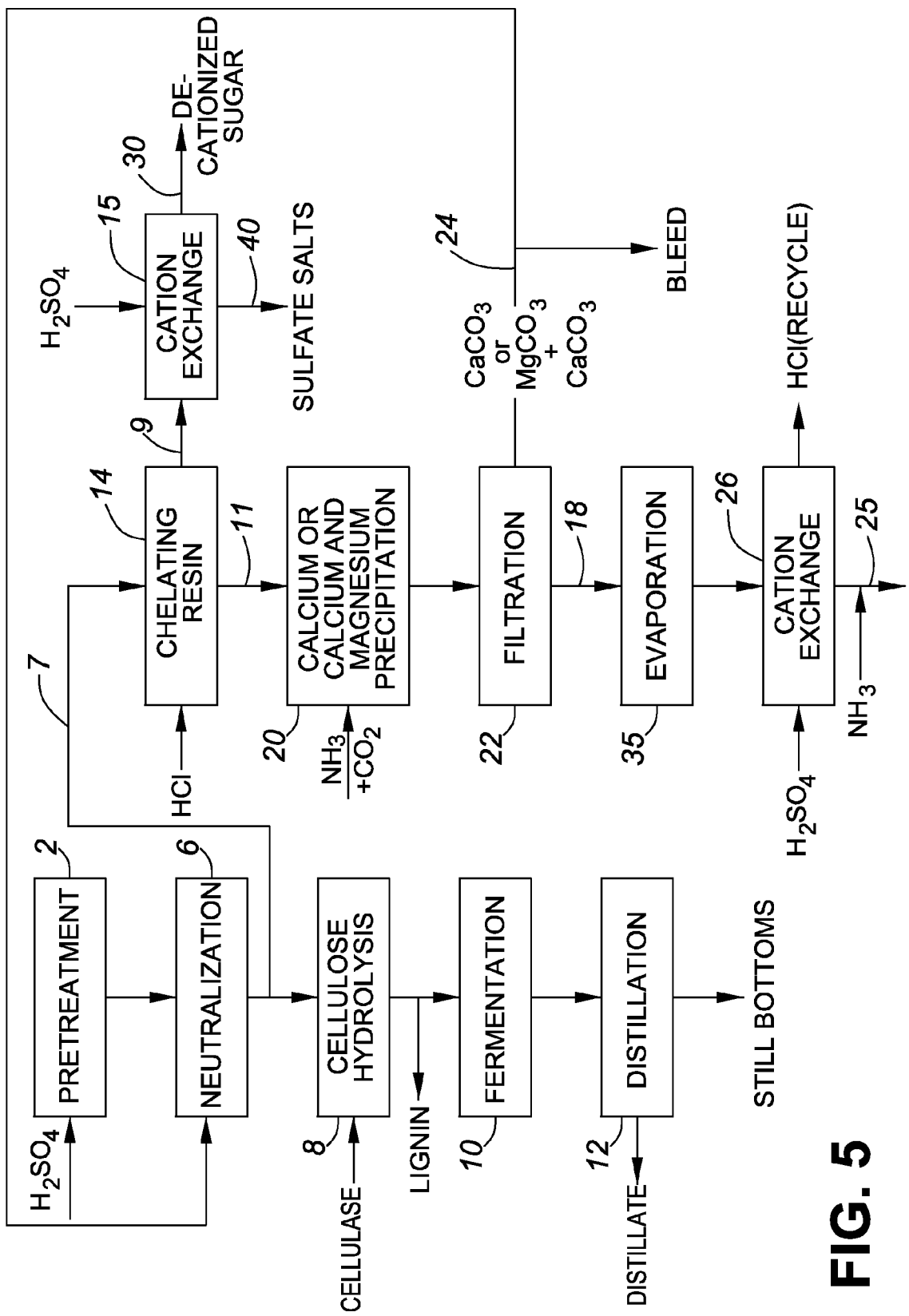
FIG. 5 is a process flow diagram for recycling a calcium carbonate-containing stream to the neutralization according to yet another embodiment of the invention. This embodiment utilizes a chelating resin to remove calcium or calcium and magnesium ions from a sugar stream obtained from a stream comprising a neutralized, pretreated feedstock. The resin bed is then regenerated with hydrochloric acid. The salt stream obtained upon regeneration of the chelating resin is treated with carbon dioxide and alkali to precipitate the calcium as calcium carbonate. After removal and recycle of the calcium carbonate to neutralization, a second cation exchange is conducted on the resulting clarified salt stream. Regeneration of this resin bed with sulfuric acid produces sulfate salts. Cation exchange using sulfuric acid as a regenerant is also conducted on a sugar stream obtained from the first cation exchange, which also produces sulfate salts.

Referring now to FIG. 5, there is shown yet another embodiment of the invention. This embodiment also employs two ion exchange operations, although, in this case, the first ion exchange utilizes a chelating resin 14 to bind calcium and magnesium ions.

According to this embodiment, the sugar stream 7 comprising ammonium sulfate, potassium sulfate, sodium sulfate, calcium sulfate and magnesium sulfate is fed to the chelating resin 14 which complexes calcium and magnesium ions. A low affinity sugar stream 9 containing reduced levels of calcium and comprising sugar, sodium sulfate, ammonium sulfate and potassium sulfate is obtained from the resin bed.

After the bed of the chelating resin 14 is saturated or nearly saturated with calcium and magnesium ions, it is regenerated by the addition of hydrochloric acid. This results in a stream 11 comprising the soluble calcium salt, calcium chloride, as well as magnesium chloride, and excess hydrochloric acid. Stream 11 is then treated with aqueous ammonia and carbon dioxide, or other alkali such as carbonates or bicarbonates, in a calcium precipitation step 20 to precipitate calcium carbonate and magnesium carbonate, which are then removed by filtration 22. A stream 24 containing calcium carbonate and magnesium carbonate is recycled to neutralization 6. A clarified salt stream 18 resulting from the filtration will comprise ammonium chloride and the stream may be subjected to evaporation 35 and fed to a cation exchanger 26 to convert the ammonium chloride to ammonium sulfate by regeneration with sulfuric acid. The hydrochloric acid produced during the feeding of the ammonium chloride stream may be recycled to regenerate the chelating resin 14.

The low affinity sugar stream 9 obtained from the chelating resin 14 contains reduced levels of calcium and comprises sugar and salts of monovalent cations, namely sodium sulfate, ammonium sulfate and potassium sulfate. Stream 9 is subsequently fed to a cation exchanger 15. As this stream is fed to the cation exchanger 15, the sodium, ammonium and potassium ions of the sulfate salts bind to the resin, while sugar and acid 30 pass through the resin bed. The cation exchanger 15 is then regenerated with sulfuric acid to obtain the product stream comprising sodium, ammonium and potassium sulfate salts 40, along with excess sulfuric acid. The addition of aqueous ammonia to the sulfate salts 40 may be carried out to convert the remaining sulfuric acid to ammonium sulfate. The result is a stream comprising ammonium sulfate, potassium sulfate and sodium sulfate.

The de-ionized stream 30 may be further processed to remove mineral acid and organic acids as discussed previously with reference to FIG. 1A. The sugars in this stream may then be fermented as discussed previously.

As used herein, the term "chelating resin" refers to a resin into which functional groups have been introduced that form chelates with calcium ions, and optionally magnesium ions if such ions are present in solution. The chelating group may be any group with two or more electron donor elements such as nitrogen, sulfur, oxygen and phosphorus. Various types of chelating resins are known in the art, including those with functional groups selected from N—O, S—N, N—N, O—O and P—N. Non-limiting examples of particularly well-known chelating resins that may be used in the practice of the invention include iminodiacetate-type and polyamine-type chelating resins. As noted previously, a chelating resin is considered a type of cation exchange resin.

Chelating resins are well known in the art and are typically used in water purification processes to remove metal contaminants from solution. An example of a preferred regenerant is an acid, such as hydrochloric acid, which forms chloride salts. Other acid regenerants may be utilized as desired to produce other soluble calcium salts. However, if sulfuric acid is used as a regenerant it must be carefully managed since this acid can produce insoluble calcium sulfate that can precipitate in the resin bed.

As will be appreciated by those of skill in the art, chelating resins may be either macroporous, i.e., contain discrete pores, or microporous (gel resins) and can contain a narrow or wide range of particle shape and size. Furthermore, the cross-linking of the polymeric structure can be varied to achieve a desired degree of porosity. A typical polymeric structure for a chelating resin is formed using divinyl benzene cross-linked polystyrene. The chelating resin may be a strong acid or weak acid cation exchange resin. Preferably, the chelating resin is a strong acid cation exchange resin.

The sulfate salts produced in the above-described embodiments are preferably used as a fertilizer, in which case they are purified by crystallization or electrodialysis, drying, or agglomeration and granulation. The purified salt can then be used as a liquid fertilizer, or alternately dried and used as a solid fertilizer or processed to recover sulfuric acid and/or alkali.

Although the recycle of calcium carbonate produced as a byproduct during sulfate salt production is described, it should be appreciated that this salt may be generated at other stages of the processing of the lignocellulosic feedstock other than those stages described above. The above-described embodiments are provided by way of example only.

It should also be appreciated that the calcium-containing stream sent to precipitation may be obtained or derived from stages of the conversion process not specifically described herein. In principle, the stream from which calcium is precipitated can be any calcium-containing stream resulting from converting the lignocellulosic feedstock to glucose, xylose, or a combination thereof. The inclusion of the embodiments set forth above is for illustrative purposes and should not be construed to limit the current invention in any manner.

The present invention will be further illustrated in the following Examples 1-3 based upon Applicants' knowledge of the process. Examples 4-7 are based on laboratory data.

EXAMPLES

Example 1

Obtaining a Calcium- and Magnesium-Containing Sugar Stream from Calcium and Magnesium Contained in a Lignocellulosic Feedstock, Recovering the Calcium as Calcium Carbonate and Magnesium as Magnesium Carbonate, and Using the Calcium Carbonate and Magnesium Carbonate for pH Control in Cellulose Hydrolysis Wheat straw (750 t/d, moisture-free basis) at 12% moisture content is received at the plant in bales. The straw contains 35.9% cellulose, 17.5% xylan, 22.1% lignin, numerous other organic compounds, and inorganic cations including, potassium at 1.1%, calcium at 0.13%, magnesium at 0.06%, and sodium at 0.01% (w/w). With reference to FIG. 1B, the bales are broken up and fed to a steam/dilute acid pretreatment system 2, as described by Foody, U.S. Pat. No. 4,461,648. After pretreatment 2, the slurry is sent over a decanter centrifuge to separate the sugar stream 4 from the pretreated solids. The sugar stream 4 has a flow rate of 121,000 L/h. The sugars in stream 4 are xylose (26 g/L), arabinose (2.5 g/L), glucose (7.4 g/L), galactose (1.7 g/L), and mannose (0.9 g/L). Other organic compounds in the sugar stream include soluble lignin (6.4 g/L), acetic acid (3.5 g/L), glucuronic acid (1.2 g/L), galacturonic acid (0.7 g/L) and furfural (2.2 g/L). The sugar stream also contains sulfuric acid (7.3 g/L), potassium (1.7 g/L), calcium (0.2 g/L), magnesium (0.12 g/L), and sodium (0.02 g/L). Those skilled in the art are aware that the sugar stream 4 also contains numerous other compounds and that obtaining a complete identification and quantification of these compounds is very difficult.

The sugar stream 4 is fed to a precipitation tank to precipitate 20 the calcium and magnesium. Carbon dioxide is added at a rate of 62.7 kg/hr to precipitate the calcium carbonate and magnesium carbonate salts. The precipitation 20 is carried out at ambient temperature in a tank of volume 40,000 liters. As the carbon dioxide reacts with calcium or magnesium, it produces sulfuric acid. A stream of 493 kg/hr of ammonia is added to neutralize the sulfuric acid and maintain a pH of 8.0 to 8.5. The neutralization of sulfuric acid with ammonia produces ammonium sulfate.

Magnesium carbonate and calcium carbonate have a solubility of less than 50 mg/L at pH 8.0. That is, the calcium and magnesium carbonate salts are predominantly insoluble since the precipitated salts form at concentrations exceeding 50 mg/L. The solubility of calcium and magnesium can be higher than this concentration, depending on the other salts that are present in the slurry. The sugar stream 34 containing the inorganic salts, calcium carbonate, magnesium carbonate, acetate salts, and ammonium sulfate, is filtered on a filter press to remove the precipitated salts and produce a dilute clarified sugar stream 30. The filter cake is produced at a rate of 318 kg/hr at 41% solids, the solids consisting of 52% calcium carbonate and 48% magnesium carbonate.

The stream 24 containing calcium carbonate and magnesium carbonate is slurried in water to a concentration of 25% solids. This stream is added at neutralization 6 with additional alkali to adjust the pH of the pretreated wheat straw to pH 5.0 prior to enzymatic hydrolysis of the cellulose 8.

Example 2

Obtaining a Calcium- and Magnesium-Containing Sugar Stream and Still Bottoms stream from the calcium and magnesium contained in a lignocellulosic feedstock, Recovering the Calcium from Each Stream as Calcium Carbonate and Magnesium as Magnesium Carbonate, and Using the Calcium Carbonate and Magnesium Carbonate for pH Control in Cellulose Hydrolysis Wheat straw (750 t/d, moisture-free basis) at 12% moisture content is received at the plant in bales. The straw contains 35.9% cellulose, 17.5% xylan, 22.1% lignin, numerous other organic compounds, and inorganic cations, including potassium at 1.1%, calcium at 0.13%, magnesium at 0.06%, and sodium at 0.01% (w/w). With reference to FIG. 1C, the bales are broken up and fed to a steam/dilute acid pretreatment system 2, as described by Foody, U.S. Pat. No. 4,461,648. The pretreated stream has a flow rate of 193,000 L/h and contains 9.5% undissolved solids. The soluble sugars in this stream are xylose (26 g/L), arabinose (2.5 g/L), glucose (7.4 g/L), galactose (1.7 g/L), and mannose (0.9 g/L). Other organic compounds in this stream include soluble lignin (6.4 g/L), acetic acid (3.5 g/L), glucuronic acid (1.2 g/L), galacturonic acid (0.7 g/L) and furfural (2.2 g/L). The stream also contains sulfuric acid (7.3 g/L), potassium (1.7 g/L), calcium (0.2 g/L), magnesium (0.12 g/L), and sodium (0.02 g/L). Those skilled in the art are aware that the pretreated stream also contains numerous other compounds and that obtaining a complete identification and quantification of these compounds is very difficult.

Stream 24 contains calcium carbonate and magnesium carbonate at a weight ratio of 52/48 in a slurry in water at a concentration of 25% solids. This stream is added at neutralization 6 at a rate of 13,340 kg/hr to adjust the pH of the pretreated wheat straw to pH 5.0 prior to enzymatic hydrolysis of the cellulose 8. The enzymatic hydrolysis is run for 96 hr at pH 5.0, 50° C. in a series of four vessels of volume 5 million liters each. The vessels are agitated with 0.8 hp/1000 gal of power input. Cellulase enzyme produced by Iogen Corporation is added to the first vessel as a liquid containing active protein. The enzyme is added at a dosage of 25 mg protein per gram cellulose.

Following hydrolysis, the slurry containing an aqueous sugar solution and unconverted solids, which are primarily lignin, are separated by a filter press into a solids stream and an aqueous stream. The aqueous stream is sent to fermentation 10 for fermentation of the glucose and xylose to ethanol. The ethanol is removed by distillation 12, resulting in still bottoms 16.

The still bottoms stream 16 is fed to a precipitation tank to precipitate 20 the remaining soluble calcium and magnesium. Carbon dioxide is added at a rate of 1602 kg/hr to precipitate the calcium carbonate and magnesium carbonate salts. The precipitation is carried out at ambient temperature in a tank of volume 40,000 liters. As the carbon dioxide reacts with calcium or magnesium, it produces sulfuric acid. A stream of 1238 kg/hr of ammonia is added to neutralize the sulfuric acid and maintain a pH of 8.0 to 8.5. The neutralization of sulfuric acid with ammonia produces ammonium sulfate.

Calcium carbonate and magnesium carbonate have a solubility of less than 50 mg/L at pH 8.0. That is, the calcium and magnesium carbonate salts are predominantly insoluble since the precipitated salts form at concentrations exceeding 50 mg/L. The solubility of calcium and magnesium can be higher than this concentration, depending on the other salts that are present in the slurry. The residual stream containing the inorganic salts, calcium carbonate, magnesium carbonate, acetate salts, and ammonium sulfate, is filtered on a filter press to remove the precipitated salts and produce a dilute clarified residual stream 30. The filter cake is produced at a rate of 8573 kg/hr at 41% solids, the solids consisting of 52% calcium carbonate and 48% magnesium carbonate. Initially, the full cake stream 24 is recycled to the neutralization after dilution to 25% solids with water. Once the calcium and magnesium concentrations accumulate to the point sufficient to neutralize the pretreated feedstock, a bleed of 3% of the cake is carried out to purge calcium and magnesium and prevent the buildup of these elements.

Example 3

Obtaining a Calcium-Containing Sugar Stream and a Still Bottoms Stream from the Calcium Contained in a Lignocellulosic Feedstock, Recovering the Calcium from Each Stream as Calcium Carbonate, and Using the Calcium Carbonate for pH Control in Cellulose Hydrolysis Wheat straw (750 t/d, moisture-free basis) at 12% moisture content is received at the plant in bales. The straw contains 35.9% cellulose, 17.5% xylan, 22.1% lignin, numerous other organic compounds, and inorganic cations, including potassium at 1.1%, calcium at 0.13%, and sodium at 0.01% (w/w). With reference to FIG. 1C, the bales are broken up and fed to a steam/dilute acid pretreatment system 2, as described by Foody, U.S. Pat. No. 4,461,648. The pretreated stream has a flow rate of 193,000 L/h and contains 9.5% undissolved solids. The soluble sugars in this stream are xylose (26 g/L), arabinose (2.5 g/L), glucose (7.4 g/L), galactose (1.7 g/L), and mannose (0.9 g/L). Other organic compounds in this stream include soluble lignin (6.4 g/L), acetic acid (3.5 g/L), glucuronic acid (1.2 g/L), galacturonic acid (0.7 g/L) and furfural (2.2 g/L). The stream also contains sulfuric acid (7.3 g/L), potassium (1.7 g/L), calcium (0.2 g/L), and sodium (0.02 g/L). Those skilled in the art are aware that the pretreated stream also contains numerous other compounds and that obtaining a complete identification and quantification of these compounds is very difficult.

Stream 24 contains calcium carbonate in a slurry in water at a concentration of 25% solids. This stream is added at neutralization 6 at a rate of 11,500 kg/hr to adjust the pH of the pretreated wheat straw to pH 5.0 prior to enzymatic hydrolysis of the cellulose 8. The enzymatic hydrolysis is run for 96 hr at pH 5.0, 50° C. in a series of four vessels of volume five million liters each. The vessels are agitated with 0.8 hp/1000 gal of power input. Cellulase enzyme produced by Iogen Corporation is added to the first vessel as a liquid containing active protein. The enzyme is added at a dosage of 25 mg protein per gram cellulose.

Following hydrolysis, the slurry containing an aqueous sugar solution and unconverted solids, which are primarily lignin, are separated by a filter press into a solids stream and an aqueous stream. The aqueous stream is sent to fermentation 10 for fermentation of the glucose and xylose to ethanol. The ethanol is removed by distillation 12, resulting in still bottoms stream 16.

The still bottoms stream 16 is fed to a precipitation tank to precipitate 20 the remaining soluble calcium. Carbon dioxide is added at a rate of 1265 kg/hr to precipitate the calcium carbonate. The precipitation is carried out at ambient temperature in a tank of volume 40,000 liters. As the carbon dioxide reacts with calcium, it produces a molecule of sulfuric acid. A stream of 978 kg/hr of ammonia is added to neutralize the sulfuric acid and maintain a pH of 8.0 to 8.5. The neutralization of sulfuric acid with ammonia produces ammonium sulfate.

Calcium carbonate has a solubility of less than 50 mg/L at pH 8.0. That is, the calcium carbonate is predominantly insoluble since precipitated calcium carbonate forms at concentrations exceeding 50 mg/L. The solubility of calcium and magnesium can be higher than this concentration, depending on the other salts that are present in the slurry. The residual stream containing the inorganic salts calcium carbonate, acetate salts, and ammonium sulfate is filtered on a filter press to remove the precipitated salts and produce a dilute clarified residual stream 30. The filter cake is produced at a rate of 7012 kg/hr at 41% solids. Initially, the full cake stream 24 is recycled to the neutralization after dilution to 25% solids with water. Once the calcium concentration accumulates to the point sufficient to neutralize the pretreated feedstock, a bleed of 1% of the cake is carried out to purge calcium and prevent the buildup of this element.

Example 4

A Summary of the Concentration of Selected Components in Sugar Streams Before and after Precipitation of Calcium Salts Using $CO_2+NH_3$ With reference to FIG. 1A, a pretreated wheat straw stream was obtained by steam/dilute acid pretreatment 2 according to the method set out by Foody in U.S. Pat. No. 4,461,648 (incorporated herein by reference). The pretreated wheat straw slurry, at about 6.5% undissolved solids, was subjected to neutralization 6 to achieve a pH of 5.0 using $CaCO_3$ (Fisher Chemicals) then vacuum-filtered through 1.6 μm glass fibre filters. The pH of the filtrate, which corresponds to sugar stream 7, was adjusted to pH 8 by adding 180 to 220 μL of aqueous ammonia (28 wt %) to 100 mL of the filtrate while maintaining the temperature at 50° C. The resulting solution was treated in precipitation 20 with carbon dioxide at 2 mL/min for ten minutes with continued addition of alkali (28 wt % aqueous ammonia, 1.44 to 2.1 mL) to maintain the solution close to pH 8 throughout the precipitation 20. The composition of selected components in the initial and final sugar solutions (corresponding to sugar streams 7 and 30, respectively in FIG. 1A) after calcium precipitation is given in Table 1 below. It should be appreciated that the sugar solutions also contain potassium, magnesium and sodium, as well as additional organic compounds including soluble lignin, glucuronic acid, galacturonic acid and furfural. However, those skilled in the art are aware that sugar streams generated in lignocellulosic conversion processes also contain numerous other compounds. The solids generated by precipitation were collected after vacuum-filtration 22 through a 1.6 μm glass fibre filter to generate a slurry containing the recovered calcium carbonate (corresponding to stream 24).

TABLE 1

|  | [calcium], g/L | pH | $CaCO_3$, g | [xylose], g/L | [glucose], g/L | [sulfate], g/L | [acetate], g/L |
|---|---|---|---|---|---|---|---|
| Neutralized feedstock stream | 2.3 | 5.0 | N/A | 28.2 | 3.5 | 8.3 | 3.8 |
| sugar stream after $CO_2 + NH_3$ | 0.3 | 8.0 | 0.8 | 27.4 | 3.4 | 8.0 | 3.6 |

Example 5

A Summary of the Concentration of Selected Components in the Initial Sugar Stream and the Final Stream after Neutralization with $CaCO_3$ Referring again to FIG. 1A, a 250 g sample of a pretreated wheat straw slurry stream (6.5% undissolved solids) obtained by steam/dilute acid pretreatment 2, as described by Foody in U.S. Pat. No. 4,461,648, was neutralized in neutralization 6 using 15.24 g of a 30% $CaCO_3$ slurry (Fisher Scientific) at 50° C. The slurry was well mixed during the neutralization 6. The composition of selected components of the initial and final sugar solutions is given in Table 2. The initial solution is obtained for analysis by filtering the slurry from pretreatment 2 through a glass fibre filter and the final solution corresponds to sugar stream 7 in FIG. 1A. As noted hereinabove, the sugar solution will also contain the additional organic compounds and ions. (See the discussion in Example 4).

TABLE 2

|  | [calcium], g/L | pH | [xylose], g/L | [glucose], g/L | [sulfate], g/L | [acetate], g/L |
|---|---|---|---|---|---|---|
| Pretreated feedstock stream | 0.3 | 1.4 | 30.1 | 3.7 | 11.2 | 4.4 |
| Sugar stream after neutralization with calcium carbonate | 2.3 | 5.0 | 30.4 | 3.8 | 11.2 | 4.6 |
| component, % of input | N/A | N/A | 100.9 | 102.2 | 100.1 | 103.9 |

Example 6

A Summary of the Concentration of Selected Components in the Initial and Final Sugar Stream after Neutralization with Recovered $CaCO_3$ With reference to FIG. 1A, a solution containing calcium salts (corresponding to stream 24) recovered from Example 4 was used to neutralize a pretreated wheat straw stream (20 g, pH 1.4) prepared by pretreatment 2 using the steam/dilute acid pretreatment described by Foody in U.S. Pat. No. 4,461,648. The neutralization 6 was conducted at 50° C. with mixing and 1.3 g of a 30 wt % $CaCO_3$ solution was required. It was noted that a small amount of evaporation occurred during the neutralization 6. It was further noted that sugar and sulfate levels remained high while acetate salts precipitated to some extent. The composition of selected components of the initial and final sugar stream (corresponding to sugar streams 7 and 30, respectively in FIG. 1A) is given in Table 3. As noted hereinabove, the sugar solution will also contain the additional organic compounds and ions (see the discussion in Example 4).

TABLE 3

|  | [calcium], g/L | pH | [xylose], g/L | [glucose], g/L | [sulfate], g/L | [acetate], g/L |
|---|---|---|---|---|---|---|
| Pretreated feedstock stream | 0.37 | 1.4 | 29.27 | 3.80 | 9.85 | 3.55 |
| Sugar stream after neutralization with recovered calcium salts | 2.70 | 5.1 | 30.34 | 3.87 | 10.39 | 2.76 |
| component, % of input | N/A | N/A | 103.7 | 101.8 | 105.5 | 77.8 |

Example 7

Hydrolysis of Pretreated Wheat Straw Neutralized with Recovered $CaCO_3$

Figure 6:
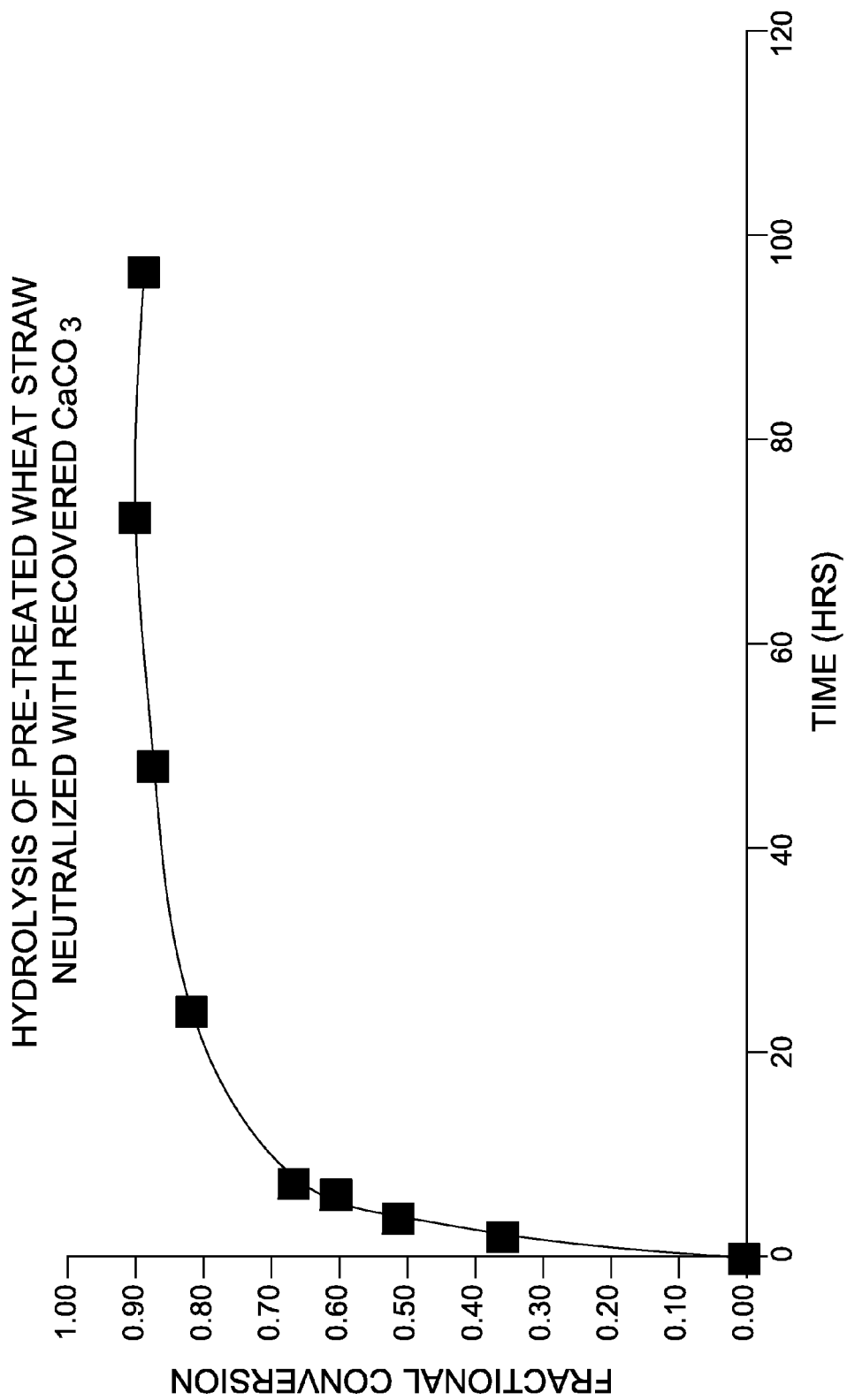
FIG. 6 shows an enzymatic hydrolysis of a pretreated lignocellulosic feedstock neutralized using $CaCO_3$ recovered according to the procedure set forth in Example 6.

Wheat straw prepared by pretreatment 2 using the steam/dilute acid pretreatment described by Foody in U.S. Pat. No. 4,461,648 and neutralized as described in Example 3 was isolated by vacuum-filtration through 1.6 μm glass fibre filters (corresponding to filtration 22 of FIG. 1A). A cellulose hydrolysis 8 of the recovered lignocellulosic feedstock using Iogen cellulase was carried out at pH 5.0 in sodium citrate buffer using a slurry of 1% cellulose and an enzyme loading of 15 mg of protein per g of cellulose. The cellulose hydrolysis 8 produces a sugar stream comprising glucose. The final pH at the end of the 96 hour hydrolysis was 4.9. The cellulose conversion as a function of time is shown in FIG. 6. Advantageously, about 90% of the cellulose was converted to glucose in this experiment.

We claim:

1. A method for processing a lignocellulosic feedstock to produce glucose, said method comprising the steps of:
    (i) pretreating the lignocellulosic feedstock with acid to produce a composition comprising pretreated feedstock;
    (ii) providing a calcium-containing stream that comprises calcium that is obtained from the lignocellulosic feedstock;
    (iii) producing a calcium carbonate-containing stream that is obtained by precipitation of said calcium from the calcium-containing stream;
    (iv) adjusting the pH of a stream comprising said pretreated feedstock with
        (a) the calcium carbonate-containing stream;
        (b) a calcium hydroxide-containing stream that is derived from said calcium carbonate-containing stream by subjecting said calcium carbonate-containing stream to calcination; or
        (c) a combination of the calcium carbonate-containing stream and the calcium hydroxide-containing stream, wherein said adjusting of the pH of said stream comprising the pretreated feedstock produces a neutralized, pretreated lignocellulosic feedstock having a pH between about 3 and about 9 and wherein the pH of the neutralized, pretreated lignocellulosic feedstock thus produced is greater than the pH of the composition comprising pretreated feedstock produced in step (i); and
    (v) carrying out enzymatic hydrolysis of said neutralized, pretreated lignocellulosic feedstock with cellulase enzymes to produce the glucose.

2. The method according to claim 1, wherein the calcium-containing stream contains magnesium that is obtained from the feedstock and wherein magnesium carbonate is produced together with calcium carbonate by precipitation of said magnesium.

3. The method according to claim 1, wherein the acid used to pretreat said lignocellulosic feedstock is sulfuric acid.

4. The method according to claim 1, wherein the enzymatic hydrolysis is carried out in the presence of a microorganism that converts glucose to at least one fermentation product.

5. The method according to claim 1, wherein the precipitation of calcium comprises the addition of carbon dioxide, alkali, carbonate or bicarbonate salts, or a combination thereof, to the calcium-containing stream.

6. The method according to claim 1, wherein the precipitation of calcium comprises the addition of carbon dioxide and an alkali selected from the group consisting of ammonia, ammonium hydroxide, sodium hydroxide, potassium hydroxide, and a combination thereof, to the calcium-containing stream.

7. The method according to claim 5, wherein the carbonate or bicarbonate salts are selected from the group consisting of ammonium carbonate, sodium carbonate, potassium carbonate, ammonium bicarbonate, sodium bicarbonate, potassium bicarbonate and a combination thereof.

8. The method according to claim 1, wherein the precipitation of calcium is carried out at a pH of about 3 to about 11, a temperature of about 20° C. to about 95° C., and a time of about 5 min to about 48 hr.

9. The method according to claim 1, wherein the calcium-containing stream, from which said calcium is precipitated, is selected from the group consisting of:
    (a') a sugar stream containing glucose, xylose, or a combination thereof;
    (b') a still bottoms stream resulting from fermenting the glucose produced in step (v) to produce a fermentation broth comprising a fermentation product, distilling the fermentation broth to obtain a stream containing a concentrated fermentation product and the still bottoms stream;
    (c') a stream resulting from combining the sugar stream and the still bottoms stream; and
    (d') a stream derived from any one of the sugar stream, the still bottoms stream and the stream resulting from combining the sugar stream and the still bottoms stream.

10. The method according to claim 9, wherein the sugar stream is obtained from the composition comprising pretreated feedstock subsequent to the step of pretreating and prior to the step of enzymatically hydrolyzing.

11. The method according to claim 1, wherein the pretreating is conducted at a pH of about 0.4 to about 3.0.

12. The method according to claim 1, wherein the pretreating is conducted to hydrolyze at least a portion of hemicellulose present in said feedstock and increase accessibility of cellulose in said feedstock to being hydrolyzed with said cellulase enzymes.

13. The method according to claim 1, wherein the pretreating is conducted at a temperature of between about 160° C. to about 280° C.

14. The method according to claim 1, wherein the cellulase enzymes comprise cellobiohydrolases (CBHs), endoglucanases (EGs) and β-glucosidase.

15. The method according to claim 1, wherein the lignocellulosic feedstock is selected from the group consisting of corn stover, soybean stover, corn cobs, rice straw, rice hulls, corn fiber, wheat straw, barley straw, canola straw, oat straw, oat hulls and combinations thereof.

16. The method according to claim 9, wherein the calcium-containing stream from which said calcium is precipitated is the still bottoms stream, or a stream derived therefrom.

17. The method according to claim 9, wherein the calcium-containing stream from which said calcium is precipitated is the stream resulting from combining the sugar stream and the still bottoms stream, or a stream derived therefrom.

18. The method according to claim 9, wherein the calcium-containing stream from which said calcium is precipitated is the sugar stream, or a stream derived therefrom.

19. The method according to claim 16, wherein, after the calcium is precipitated, a sugar-containing stream is obtained with a reduced concentration of calcium, which sugar-containing stream is fermented to produce an alcohol, a sugar alcohol, an organic acid, or a combination thereof.

20. The method according to claim 1, wherein the neutralized, pretreated lignocellulosic feedstock has a pH between about 4 and about 6.

* * * * *